US010428101B2

(12) United States Patent
Chen et al.

(10) Patent No.: US 10,428,101 B2
(45) Date of Patent: Oct. 1, 2019

(54) PREPARATION OF GLYCOSPHINGOSINES

(71) Applicant: The Regents of the University of California, Oakland, CA (US)

(72) Inventors: Xi Chen, Davis, CA (US); Hai Yu, Woodland, CA (US); Joel Hwang, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/897,596

(22) PCT Filed: Jun. 16, 2014

(86) PCT No.: PCT/US2014/042530
§ 371 (c)(1),
(2) Date: Dec. 10, 2015

(87) PCT Pub. No.: WO2014/201462
PCT Pub. Date: Dec. 18, 2014

(65) Prior Publication Data
US 2016/0222048 A1 Aug. 4, 2016

Related U.S. Application Data

(60) Provisional application No. 61/835,249, filed on Jun. 14, 2013.

(51) Int. Cl.
*C07H 15/04* (2006.01)
*C07H 1/00* (2006.01)
*C07H 15/08* (2006.01)
*C12P 19/04* (2006.01)
*C12P 19/18* (2006.01)
*C12P 19/44* (2006.01)

(52) U.S. Cl.
CPC .............. *C07H 15/04* (2013.01); *C07H 1/00* (2013.01); *C07H 15/08* (2013.01); *C12P 19/04* (2013.01); *C12P 19/18* (2013.01); *C12P 19/44* (2013.01); *C07B 2200/11* (2013.01)

(58) Field of Classification Search
CPC .......... C07H 15/04; C07H 1/00; C07H 15/08
USPC ......................................................... 435/74
See application file for complete search history.

(56) References Cited

U.S. PATENT DOCUMENTS

| 9,102,967 | B2* | 8/2015 | Chen ........................ C12P 19/44 |
| 2001/0007760 | A1 | 7/2001 | Palcic et al. |
| 2004/0082792 | A1 | 4/2004 | Wipf et al. |
| 2005/0032742 | A1* | 2/2005 | DeFrees .................. C12P 19/18 |
| | | | 514/54 |
| 2006/0127950 | A1 | 6/2006 | Bosques et al. |
| 2012/0225797 | A1 | 9/2012 | Northen et al. |

FOREIGN PATENT DOCUMENTS

WO    2012/167088 A1    12/2012

OTHER PUBLICATIONS

Thon et al., PmST2: A novel Pasteurella multocida glycolipid α2-3-sialyltransferase. Glycobiology vol. 21 No. 9, pp. 1206-1216, 2011. doi:10.1093/glycob/cwr054 Advance Access publication on Apr. 21, 2011. (Year: 2011).*
Zhang et al. "Fluorous tagging strategy for solution-phase synthesis of small molecules, peptides, and oligosaccharides," Curr Opin Drug Discov Devel., vol. 7, pp. 784-797 (2004).
International Search Report for International Application No. PCT/US2014/042530 dated Nov. 4, 2014.
Zhang, et al., "Synthetic applications of fluorous solid-phase extraction (F-SPE)," Tetrahedron, vol. 62, pp. 11837-11865 (2006).
Jaipuri, et al., "Toward solution-phase automated iterative synthesis: fluorous-tag assisted solution-phase synthesis of linear and branched mannose oligomers," Org. Biomol. Chem., vol. 6, pp. 2686-2691 (2008).
Pohl, "Automated Solution-Phase Oligosaccharide Synthesis and Carbohydrate Microarrays: Development of Fluorous-based tools for Glycomics," Chemical Glycobiology; Chen, X., Halcomb, R., Wang, P. G., Eds.; ACS Symposium Series 990; American Chemical Society: Washington, DC, pp. 272-287 (2008).
Manzoni, "Rapid synthesis of oligosaccharides using an anomeric fluorous silyl protecting group," Chem. Commun., pp. 2930-2931 (2003).
Manzoni, et al., "Synthesis of the Lewis a Trisaccharide Based on an Anomeric Silyl Fluorous Tag.," Org. Lett., vol. 6, pp. 4195-4198 (2004).
Zong, et al., "Fluorous Supported Modular Synthesis of Heparan Sulfate Oligosaccharides," Org. Lett., vol. 15, pp. 342-345 (2013).
Manzoni, et al., "A New Fluorous Protective Group for Peptide and Oligosaccharide Synthesis," Org. Lett., vol. 8, pp. 955-957 (2006).
Zhang, et al., "Synthesis and Applications of a Light-Fluorous Glycosyl Donor," J. Org. Chem., vol. 74, pp. 2594-2597 (2009).
Carrel, et al., "Cap-and-Tag Solid Phase Oligosaccharide Synthesis," J. Org. Chem., vol. 73, pp. 2058-2065 (2008).
Jing, et al., "Fluorous thiols in oligosaccharide synthesis," Tetrahedron Lett., vol. 45, pp. 4615-4618 (2004).
Park, et al., "Mono-Vs. di-flourous tagged glucosamines for iterative oligosaccharide synthesis," J. Fluor. Chem., vol. 129, pp. 978-982 (2008).
Ko, et al., "Fluorous-based Carbohydrate Microarrays," J. Am. Chem. Soc., vol. 127, pp. 13162-13163 (2005).
Jaipuri, et al., "Synthesis and Quantitative Evaluation of Glycero-D-manno-heptose Binding to Concanavalin A by Fluorous-Tag Assistance," Angew. Chem. Int. Ed., vol. 47, pp. 1707-1710 (2008).
Chen, et al., "Synthesis of Fluorous Tags for Incorporation of Reducing Sugars into a Quantitative Microarray Platform," Org. Lett., vol. 10, pp. 785-788 (2008).

(Continued)

Primary Examiner — Yih-Horng Shiao
(74) Attorney, Agent, or Firm — Kilpatrick Townsend and Stockton LLP

(57) ABSTRACT

The present invention provides a method of preparing an isolated oligosaccharide or glycolipid by preparing the oligosaccharide or glycolipid having a hydrophobic group, such as a perfluorinated alkyl or a fatty acid, and separating the oligosaccharide or glycolipid using a solid-phase extraction cartridge.

14 Claims, 6 Drawing Sheets

(56) References Cited

OTHER PUBLICATIONS

Edwards, et al., "Probing the limitations of the fluorous content for tag-mediated microarray formation," *Chem. Commun.*, vol. 48, pp. 510-512 (2012), with Electronic Supplementary Information (ESI), pp. SI-1-SI-31 (2011).
Kasuya, et al., "Fluorous-tagged compound: a viable scaffold to prime oligosaccharide synthesis by cellular enzymes," *Biochem. Biophys. Res. Commun.*, vol. 316, pp. 599-604 (2004).
Kasuya, et al., "Fluorous tag method for the simultaneous synthesis of different kind of glycolipids," *J. Fluor. Chem.*, vol. 131, pp. 655-659 (2010).
Kasuya, et al., "Evaluation of the hydrophobicity of perfluoroalkyl chains in amphiphilic compounds that are incorporated into cell membrane," *J. Fluor. Chem.*, vol. 132, pp. 202-206 (2011).
Kasuya, et al., "Cellular Uptake and Saccharide Chain Elongation of "Fluoro-amphiphilic" Glycosides," *Chem. Lett.*, vol. 34, pp. 856-857 (2005).
Tojino, et al., "Immobilization of fluorous oligosaccharide recognized by influenza virus on polytetrafluoroethylene filter," *Bioorg. Chem. Lett.*, vol. 22, pp. 1251-1254 (2012).
Northen, et al., "A nanostructure-initiator mass spectrometry-based enzyme activity assay," *Proc. Natl. Acad. Sci.*, vol. 105, pp. 3678-3683 (2008).
Deng, et al., "Encoding substrates with mass tags to resolve stereospecific reactions using Nimzyme," *Rapid Commun. Mass Spectrom.*, vol. 26, pp. 611-615 (2012).
Liu, et al., "Chemoenzymatic Design of Heparan Sulfate Oligosaccharides," *J. Biol. Chem.*, vol. 285, pp. 34240-34249 (2010).

\* cited by examiner

Figure 1
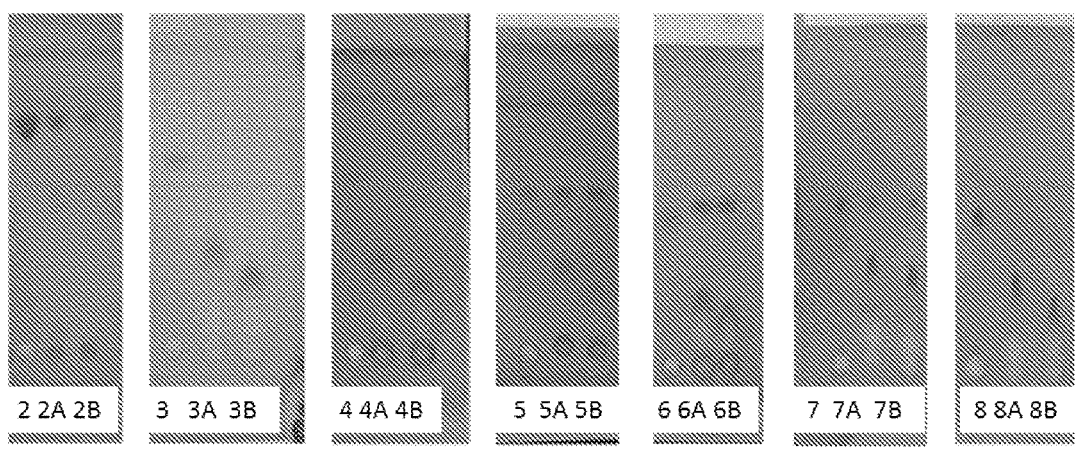
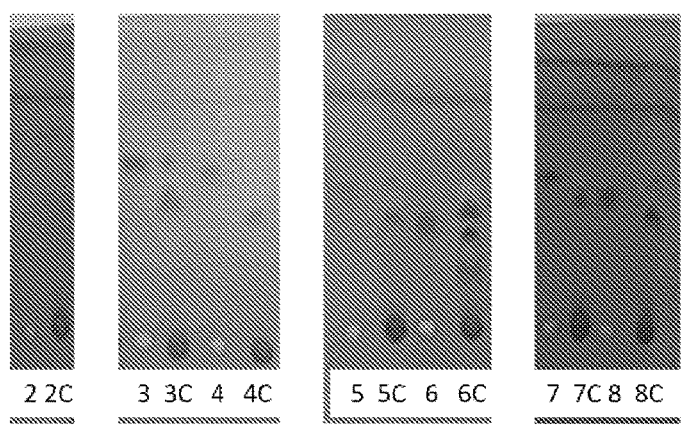

PREPARATION OF GLYCOSPHINGOSINES

CROSS-REFERENCE TO RELATED APPLICATIONS

This application is the U.S. National Stage Entry under § 371 of International Application No. PCT/US2014/042530, filed Jun. 16, 2014, which claims priority to U.S. Provisional Application No. 61/835,249, filed Jun. 14, 2013, which is incorporated in its entirety herein.

STATEMENT AS TO RIGHTS TO INVENTIONS MADE UNDER FEDERALLY SPONSORED RESEARCH AND DEVELOPMENT

This invention was made with Government support under Grant Nos. CHE-1012511 and CHE-1300449 by the National Science Foundation. The Government has certain rights in this invention.

BACKGROUND OF THE INVENTION

Carbohydrates are biologically important but synthetically challenging biomolecules. Fluorous-tagged glycans with an oligo(ethylene glycol) linker are well tolerated glycosyltransferase substrates for high-yield one-pot multi-enzyme (OPME) synthesis and facile fluorous solid-phase extraction (FSPE) purification of glycans.

Oligo(ethylene glycol)-linked light fluorous tags have been found to be optimal for conjugating to glycans for both high-yield enzymatic glycosylation reactions using OPME systems and quick product purification by FSPE cartridges. The combination of OPME glycosylation systems and the FSPE cartridge purification scheme provides a highly effective strategy for facile synthesis and purification of glycans.

Tagging organic compounds with a light fluorous tail such as a perfluorooctyl ($C_8F_{17}$) or perfluorohexyl ($C_6F_{13}$) group followed by product purification using fluorous solid-phase extraction (FSPE) has found increasing synthetic uses. For carbohydrate synthesis, non-cleavable single, double, and cleavable fluorous tags have been used in the acceptor glycans to allow solution-phase synthesis and fast product purification. Light fluorous protecting groups have also been used in solution-phase or solid-phase synthesis. Odorless fluorinated thioglycosyl donors were prepared and shown excellent reactivities in glycosylation reactions. Mono-perfluoroalkyl (e.g. $C_8F_{17}$- and $C_6F_{13}$) tags and a di-$C_6F_{13}$-tag allowed non-covalent immobilization of fluorous-tagged monosaccharides and oligosaccharides on fluorocarbon-coated glass slides to generate glycan microarrays that can sustain washing processes in carbohydrate-lectin binding studies.

Except for a limited number of examples (e.g. feeding cultured animal cells with fluorous-tagged lactosides or an N-acetylglucosaminide for producing small amounts of elongated fluorous oligosaccharides, using a $C_3F_7$ tag to facilitate the product purification of enzymatically synthesized heparosan oligosaccharide derivatives, and using non-covalently immobilized light fluorous tagged glycans as substrates for glycosyltransferase and glycosidase activity assays by mass spectrometry), light fluorous tags have not been used broadly to facilitate product purification in preparative-scale enzymatic synthesis.

Without being bound by theory, this is most likely due to either the lower tolerance of relatively long fluorous tags (e.g. a $C_8F_{17}$ or longer tag) by enzymatic reactions which often leads to no reaction or low yields, or the lower efficiency in FSPE cartridge-purification inherited by very short fluorous tags (e.g. a $C_3F_7$ tag).

Accordingly, there is a need to develop OPME systems that tolerate long fluorous tags, which would enable FSPE on a preparative scale. The present disclosure provides a solution to this need.

BRIEF SUMMARY OF THE INVENTION

In one embodiment, the present invention provides a method of preparing an isolated oligosaccharide or glycolipid. The method comprises forming a reaction mixture comprising an acceptor sugar linked to a hydrophobic moiety via a linker, a sugar donor, and a glycosyltransferase, under conditions suitable to form a glycosidic bond between the acceptor sugar and the sugar donor to form an oligosaccharide or glycolipid. The reaction mixture is contacted with a solid-phase extraction (SPE) cartridge under conditions sufficient to isolate the oligosaccharide or glycolipid.

BRIEF DESCRIPTION OF THE DRAWINGS

FIG. 1 shows reaction conversion rates of Table 1 and Table 2 were determined by first staining the TLC plates with p-anisaldehyde sugar stain and then using ImageQuant 5.2 to compare the relative intensities (under greyscale) between the glycosylation product spot and the lactoside acceptor spot of each reaction. For external standard comparison, each lactoside acceptor spot was also compared with its corresponding standard 10 mM stock solution spot (of compounds 2-8) to verify the conversion rates of each reaction. A: One-pot two-enzyme sialylation reaction with PmST1 E271F/R313Y. B: One-pot two-enzyme sialylation reaction with Pd2,6ST. C: One-pot four-enzyme galactosylation reaction with α1-3GalT.

DETAILED DESCRIPTION OF THE INVENTION

I. General

Figure 2:
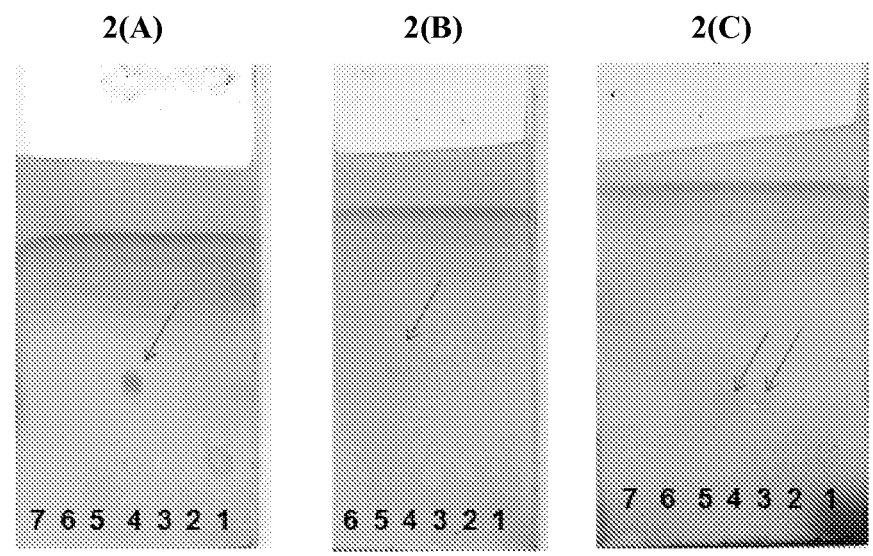
FIGS. 2(A)-(C) show FSPE purification of (A) Neu5Acα2-3LacβProNH—$C_8F_{17}$, (B) Neu5Acα2-3LacβProNH—$C_6F_{13}$, and (C) Neu5Acα2-3LacβProNH—$C_3F_7$. After loading the reaction mixture to FSPE cartridge, 3×3.5 mL of $H_2O$ (numbers 1-3) was used to wash out non-fluorous components of the mixture. 3-4×3.5 mL of MeOH (numbers 4-7) was then used to elute the fluorous-tagged glycans. As shown on thin-layer chromatography (TLC) plates, the $C_3F_7$-tagged sialoside was not retained in the cartridge during the third water wash and eluted prematurely prior to the methanol wash. Developing solvent used for TLC was EtOAc:MeOH:$H_2O$=5:2:1 by volume.
Figure 3:
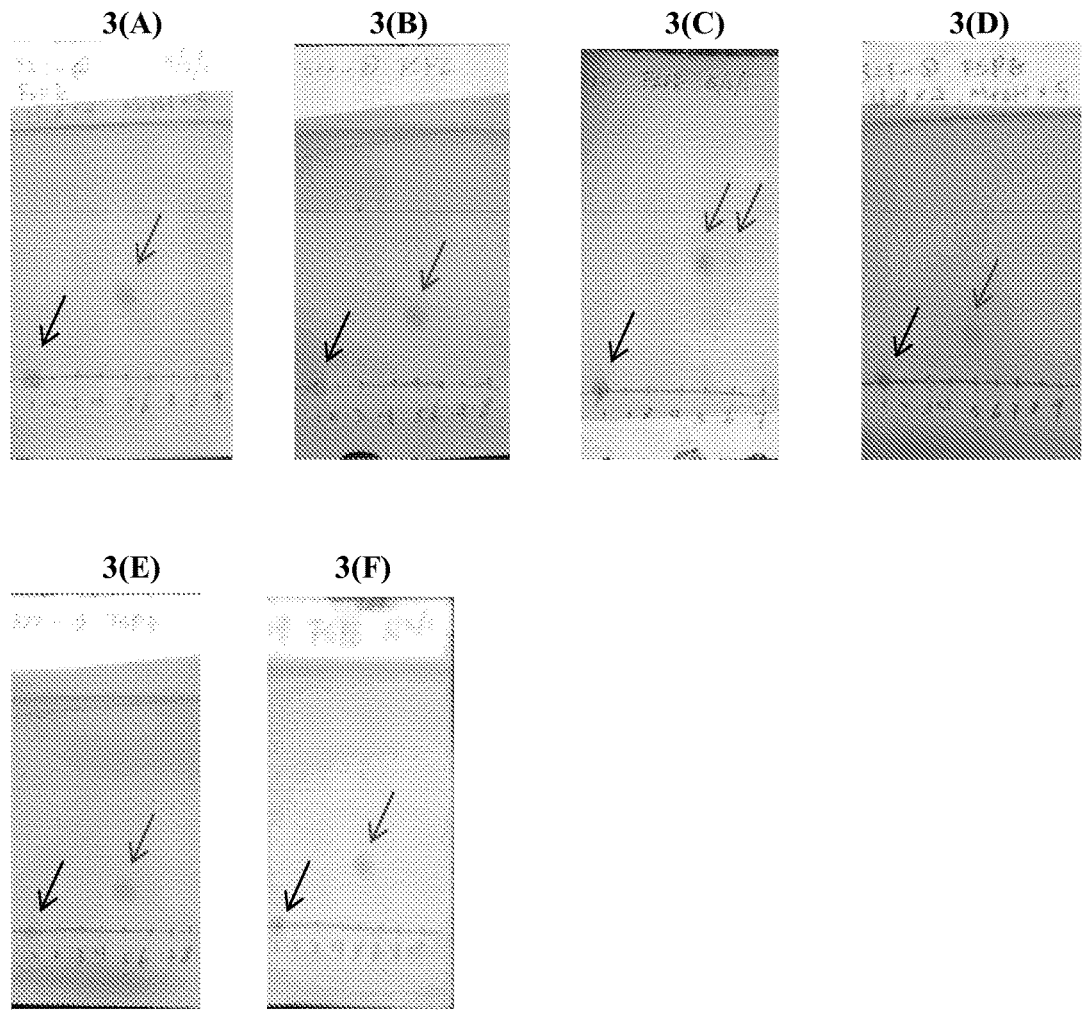
FIGS. 3(A)-(F) show FSPE purification of (A) Neu5Acα2-3LacβProNH—$C_6F_{13}$ (11), (B) Neu5Acα2-6LacβProNH—$C_6F_{13}$ (14), (C) Galα1-3LacβProNH-TEG-$C_8F_{17}$ (23), (D) Neu5Acα2-3LacβProNH-TEG-$C_6F_{13}$ (25), (E) Neu5Acα2-6LacβProNH-TEG-$C_6F_{13}$ (27), and (F) Galα1-3LacβProNH-TEG-$C_6F_{13}$ (29) monitored by thin-layer chromatography (TLC). After loading reaction mixtures to FSPE cartridges, 4×3.5 mL of $H_2O$ was used to wash out non-fluorous components of the mixture (numbers 1-4). 3-5×3.5 mL of MeOH was then used to elute the fluorous-tagged glycans (numbers 5-9). Developing solvent used for TLC was EtOAc:MeOH:$H_2O$=5:2:1 by volume. (arrows pointing to baseline spots: fluorous-tagged product. Other arrows: reaction components without fluorous tag.)

The present invention provides methods of preparing oligosaccharides containing hydrophobic moieties linked to an acceptor sugar by a linker. In particular, when the hydrophobic moiety is a perfluoroalkyl group, oligosaccharides can be purified on fluorous solid phase extraction columns on a preparative scale. The hydrophobic moiety and linker can be subsequently cleaved chemically.

II. Definitions

As used herein, the term "glycosyltransferase" refers to a polypeptide that catalyzes the formation of a glycoside or an oligosaccharide from a donor substrate or sugar donor and an acceptor or acceptor sugar. In general, a glycosyltransferase catalyzes the transfer of the monosaccharide moiety of the donor substrate to a hydroxyl group of the acceptor. The covalent linkage between the monosaccharide and the acceptor sugar can be a 1-4 linkage, a 1-3 linkage, a 1-6-linkage, a 1-2 linkage, a 2-3-linkage, a 2-6-linkage, a 2-8-linkage, or a 2-9-linkage. The linkage may be in the α- or β-configuration with respect to the anomeric carbon of the monosaccharide. Other types of linkages may be formed by the glycosyltransferases in the methods of the invention. Glycosyltransferases include, but are not limited to, sialyltransferases, heparosan synthases (HSs), glucosaminyltransferases, N-acetylglucosaminyltransferases, glucosyltransferases, glucuronyltransferases, N-acetylgalactosaminyltransferases, galactosyltransferases, galacturonyltransferases, fucosyltransferases, mannosyltransferases, xylosyltransferases. Sialyltransferases are enzymes that catalyze the transfer of sialic acid, or analogs thereof, to a monosaccharide or an oligosaccharide. In some embodiments, the glycosyltransferases useful in the present invention include those in Glycosyltransferase families 80, 29, 4, 38, 42, and 52 (GT80, GT29, GT4, GT38, GT42, and GT52 using CAZy nomenclature). GT29, GT42, GT52, and GT80 families glycosyltransferases include beta-galactoside alpha-2,3-sialyltransferases that catalyze the following conversion: CMP-sialic acid+β-D-galactosyl-R=CMP+α-sialic acid-(2→3)-D-galactosyl-R, where the acceptor is Galβ-R, where R is H, a monosaccharide, an oligosaccharide, a polysaccharide, a glycopeptide, a glycoprotein, a glycolipid, or another glycoside. GT29, GT42, and GT80 families sialyltransferases also include galactoside or N-acetylgalactosaminide alpha-2,6-sialyltransferases that catalyze the following conversion: CMP-sialic acid+galactosyl/GalNAc-R=CMP+α-sialic acid-(2→6)-D-galactosyl/GalNAc-R, where the acceptor is Gal-R or GalNAc-R, where R is H, a monosaccharide, an oligosaccharide, a polysaccharide, a glycopeptide, a glycoprotein, a glycolipid, or another glycoside. GT29 and GT42 families sialyltransferases also include sialyl alpha-2,8-sialyltransferases that catalyze the following conversion: CMP-sialic acid+Sia-OR=CMP+α-sialic acid-(2→8)-α-D-sialyl-R, where the acceptor is Sia-R, where R is H, a monosaccharide, an oligosaccharide, a polysaccharide, a glycopeptide, a glycoprotein, a glycolipid, or another glycoside. GT4 family sialyltransferases include galactosyl or glucosyl alpha-2,6-sialyltransferases that catalyze the following conversion: CMP-sialic acid+galactosyl/glucosyl-R=CMP+α-sialic acid-(2→6)-α-D-galactosyl/glucosyl-R, where the acceptor is Gal-R or Glc-R, where R is H, a monosaccharide, an oligosaccharide, a polysaccharide, a glycopeptide, a glycoprotein, a glycolipid, or another glycoside. GT38 family sialyltransferase include sialyl alpha-2,8-sialyltransferases and alpha-2,9-sialyltransferases that catalyze the following conversion: CMP-sialic acid+sialyl-R=CMP +α-sialic acid-(2→8/9)-α-D-sialyl-R, where the acceptor is Sia-R, where R is H, a monosaccharide, an oligosaccharide, a polysaccharide, a glycopeptide, a glycoprotein, a glycolipid, or another glycoside. Other suitable glycotransferases are disclosed in Li Y, Chen X. *Appl. Microbiol. Biotechnol.* 2012, 94, 887-905.

As used herein, the term "perfluorinated" refers to a hydrophobic group having each of its C—H bonds replaced by C—F bonds. For example, a perfluorinated C₆H₁₄ group would have the formula C₆F₁₄.

As used herein, the term "contacting" refers to the process of bringing into contact at least two distinct species such that they can react. It should be appreciated, however, the resulting reaction product can be produced directly from a reaction between the added reagents or from an intermediate from one or more of the added reagents which can be produced in the reaction mixture.

As used herein, the term "alpha2-3-sialidase" refers to an enzyme that catalyzes the hydrolysis of alpha2-3-glycosidic linkages of terminal sialic acids on oligosaccharides or glycoconjugates.

As used herein, the terms "polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

As used herein, the term "oligosaccharide" refers to a compound containing at least two sugars covalently linked together. Oligosaccharides include disaccharides, trisaccharides, tetrasachharides, pentasaccharides, hexasaccharides, heptasaccharides, octasaccharides, and the like. Covalent linkages generally consist of glycosidic linkages (i.e., C—O—C bonds) formed from the hydroxyl groups of adjacent sugars. Linkages can occur between the 1-carbon and the 4-carbon of adjacent sugars (i.e., a 1-4 linkage), the 1-carbon and the 3-carbon of adjacent sugars (i.e., a 1-3 linkage), the 1-carbon and the 5-carbon of adjacent sugars (i.e., a 1-5 linkage), the 1-carbon and the 6-carbon of adjacent sugars (i.e., a 1-6 linkage), the 1-carbon and the 2-carbon of adjacent sugars (i.e., a 1-2 linkage), the 1-carbon and the 1-carbon of adjacent sugars (i.e., a 1-1 linkage), the 2-carbon and the 3-carbon of adjacent sugars (i.e., a 2-3 linkage), the 2-carbon and the 6-carbon of adjacent sugars (i.e., a 2-6 linkage), the 2-carbon and the 8-carbon of adjacent sugars (i.e., a 2-8 linkage), the 2-carbon and the 9-carbon of adjacent sugars (i.e., a 2-9 linkage). A sugar can be linked within an oligosaccharide such that the anomeric carbon is in the α- or β-configuration. The oligosaccharides prepared according to the methods of the invention can also include linkages between carbon atoms other than the 1-, 2-, 3-, 4-, 5-, 6-, 8-, and 9-carbons.

As used herein, the phrase "acceptor sugar" refers to any sugar, including monosaccharides and polysaccharides, that is capable of reacting with a hydrophobic moiety to form a compound that can further react with a glycotransferase and a monosaccharide. The acceptor sugar can react with the hydrophobic moiety at any available free hydroxyl group. For example, the acceptor sugar can be a lactoside that can react with a perfluoro $C_8$ aliphatic group. The term acceptor sugar can refer to just the sugar portion of a molecule or to a sugar already attached to a linker and hydrophobic moiety.

As used herein, the phrase "hydrophobic moiety" refers to a molecular fragment that has little to no aqueous solubility. The hydrophobic moiety can comprise lipids including phospholipids, fatty acids and their esters, fatty alcohols and their esters, and perfluorinated hydrocarbons. The lipid can comprise any animal or plant derived lipid, including short chain fatty acids (having fewer than 6 aliphatic carbons), medium chain fatty acids (having 6 to 12 aliphatic carbons), and long chain fatty acids (having 13 to 21 carbons). The lipids can contain any combination of saturated or unsaturated carbon-carbon bonds. The unsaturated carbon-carbon bonds can be cis, trans, or any combination thereof. The lipids can be straight-chained or branched.

As used herein, the term "linker" refers to a molecular fragment that connects an acceptor sugar to a hydrophobic moiety. The linker typically has higher water solubility than the hydrophobic moiety. An exemplary linker is a polyethylene glycol moiety containing from 1 to 10 ($CH_2CH_2O$) units. The polyethylene glycol units in the linker can be bonded to the hydrophobic moiety and the acceptor sugar through any carbonyl-containing group, including, without limitation, amides, carbonyl, ester, urea, thiourea, and combinations thereof.

As used herein, the term "sugar donor" refers to any monosaccharide capable of reacting with an acceptor sugar and a glycotransferase to form a covalent bond between the sugar donor and the acceptor sugar. Monosaccharides that are suitable sugar donors include, without limitation, dioses such as glycoaldehyde; trioses such as D and L-glyceraldehyde; tetroses such as D and L-erythrose, threose, and erythrulose; pentoses such as D and L-arabinose, lyxose, ribose, xylose, ribulose, and xylulose; hexoses such as D and L-allose, altrose, glucose, mannose, gulose, idose, galactose, fructose, and talose; aminosugars such as N-acetylglucosamine, galactosamine, glucosamine, sialic acid, and D and L-duanosamine; and sulfosugars such as sulfoquinovose.

As used herein, the phrase "solid-phase extraction cartridge" or "SPE cartridge" refers to the cartridge used in any solid phase chromatography system capable of separating and purifying compounds containing perfluorinated or hydrophobic groups.

As used herein, the term "isolate" or "isolated" refers to obtaining a substance such as an oligosaccharide or glycolipid free of solvent and impurities. The isolated substance can be up to 70% pure, 80% pure, 90% pure, 95% pure, 97% pure, 99% pure, or 99.9% pure.

As used herein, the term "forming" refers to the bringing together reactants in a suitable reaction container together with substances that do not react but have beneficial properties. The reactants can include an acceptor sugar linked to a hydrophobic moiety via a linker, a sugar donor, and a glycosyltransferase. Substances that do not react but have beneficial properties include, without limitation, catalysts, co-solvents, surfactants, detergents, buffers, etc.

As used herein, the term "alkyl" refers to a saturated hydrocarbon radical which may be straight-chain or branched-chain (for example, ethyl, isopropyl, t-amyl, or 2,5-dimethylhexyl). This definition applies both when the term is used alone and when it is used as part of a compound term, such as "arylalkyl," "alkylamino," "alkylheteroaryl," "alkylheterocycloalkyl" and similar terms. In some embodiments, alkyl groups are those containing 1 to 24 carbon atoms. All numerical ranges in this specification and claims are intended to be inclusive of their upper and lower limits. Additionally, the alkyl and heteroalkyl groups may be attached to other moieties at any position on the alkyl or heteroalkyl radical which would otherwise be occupied by a hydrogen atom (such as, for example, 2-pentyl, 2-methylpent-1-yl and 2-propyloxy). Divalent alkyl groups may be referred to as "alkylene," and divalent heteroalkyl groups may be referred to as "heteroalkylene". The alkyl, alkylene, and heteroalkylene moieties may also be optionally substituted with halogen atoms, or other groups such as oxo, cyano, nitro, alkyl, alkylamino, carboxyl, hydroxyl, alkoxy, aryloxy, and the like.

As used herein, the term "alkenyl" refers to either a straight chain or branched hydrocarbon of 2 to 24 carbon atoms, having at least one double bond. Examples of alkenyl groups include, but are not limited to, vinyl, propenyl, isopropenyl, butenyl, isobutenyl, butadienyl, pentenyl or hexadienyl.

As used herein, the term "cycloalkyl" refers to a saturated or partially unsaturated, monocyclic, fused bicyclic or bridged polycyclic ring assembly containing from 3 to 24 ring atoms, or the number of atoms indicated For example, $C_{3-8}$ cycloalkyl includes cyclopropyl, cyclobutyl, cyclopentyl, cyclohexyl, cycloheptyl, and cyclooctyl. The cycloalkyl can also be optionally substituted with alkyl groups, thus for example $C_{3-8}$ cycloalkyl also includes methylcyclopentane and methylcyclohexane.

As used herein, the term "aryl" refers to a monocyclic or fused bicyclic, tricyclic or greater, aromatic ring assembly containing 6 to 24 ring carbon atoms. For example, aryl can be phenyl, benzyl or naphthyl, preferably phenyl. "Arylene" means a divalent radical derived from an aryl group. Aryl groups can be mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkylene-phenyl is 2,3-dihydrobenzofuran-5-yl.

As used herein, the term "fatty acid" refers to a carboxylic acid having a straight or branched, saturated, aliphatic carbon chain from 3 to 21 carbon atoms in length.

As used herein, the term "sphingosine" refers to the fragment (2S,3R)-2-aminooctadec-4-ene-1,3-diol, as well as enantiomers thereof and O- and N-alkylated, acylated, and arylated derivatives thereof. The sphingosine may be connected to the sugar or linker through an oxygen or nitrogen atom.

As used herein, the term "ceramide" refers to a compound composed of a sphingosine and a fatty acid. The fatty acid can be attached to either the oxygen or nitrogen on the sphingosine moiety. Exemplary ceramides have the fatty acid attached to the nitrogen atom of sphingosine through an amide bond.

III. Methods of Preparing Isolated Oligosaccharides

The present invention provides a method of preparing an isolated oligosaccharide or glycolipid by preparing the oligosaccharide or glycolipid having a hydrophobic group, such as a perfluorinated alkyl or a fatty acid, and separating the oligosaccharide or glycolipid using a solid-phase extraction cartridge. In one embodiment, the present invention provides a method of preparing an isolated oligosaccharide or glycolipid, including a step (a) of forming a reaction mixture having an acceptor sugar linked to a hydrophobic moiety via a linker, a sugar donor, and a glycosyltransferase, under conditions suitable to form a glycosidic bond between the acceptor sugar and the sugar donor to form an oligosaccharide or glycolipid. The method also includes a step (b) of contacting the reaction mixture with a solid-phase extraction (SPE) cartridge under conditions sufficient to isolate the oligosaccharide or glycolipid.

Any suitable hydrophobic moiety is useful in the methods of the present invention. A hydrophobic moiety is generally defined as a compound that is poorly water soluble. For example, the hydrophobic moiety can include, but is not limited to, a long-alkyl chain, a long-alkenyl chain, a lipid, a fatty acid, a fatty ester, or a perfluorinated moiety. Suitable lipids include, but are not limited to, a fatty acid, a fatty ester, a cholesterol, a triglyceride, a sphingosine, a ceramide, and a phospholipid, among others.

A fatty acid refers to a carboxylic acid having an aliphatic tail, typically from 4 to 30 carbon atoms long. Fatty acids can be saturated, mono-unsaturated or poly-unsaturated. Fatty acids useful in the present invention also include branched fatty acids such as iso-fatty acids. Examples of fatty acids useful in the present invention, include, but are not limited to, butyric acid (C4), caproic acid (C6), caprylic acid (C8), capric acid (C10), lauric acid (C12), myristic acid (C14), palmitic acid (C16), palmitoleic acid (C16), stearic acid (C18), isostearic acid (C 18), oleic acid (C 18), vaccenic acid (C 18), linoleic acid (C 18), alpha-linoleic acid (C 18), gamma-linolenic acid (C 18), arachidic acid (C20), gadoleic acid (C20), arachidonic acid (C20), eicosapentaenoic acid (C20), behenic acid (C22), erucic acid (C22), docosahexaenoic acid (C22), lignoceric acid (C24) and hexacosanoic acid (C26). Fatty acid esters are fatty acids esterified with a $C_{1-12}$ alkyl.

Other lipids include fatty alcohol, which refers to an alcohol having an aliphatic tail, typically from 4 to 30 carbon atoms long. Fatty alcohols can be saturated, mono-unsaturated or poly-unsaturated. Additional fatty alcohols useful in the present invention include branched fatty alcohols. Examples of fatty alcohols useful in the present invention, include, but are not limited to, capryl alcohol (C8), pelargonic alcohol (C9), capric alcohol (C10), lauryl alcohol (C12), myristyl alcohol (C14), cetyl alcohol (C16), palmitoleyl alcohol (C16), stearyl alcohol (C 18), isostearyl alcohol (C 18), elaidyl alcohol (C 18), oleyl alcohol (C 18), linoleyl alcohol (C 18), elaidolinoleyl alcohol (C 18), linolenyl alcohol (C 18), ricinoleyl alcohol (C 18), arachidyl alcohol (C20), behenyl alcohol (C22), erucyl alcohol (C22), lignoceryl alcohol (C24), ceryl alcohol (C26), montanyl alcohol/cluytyl alcohol (C28), myricyl alcohol/melissyl alcohol (C30) and geddyl alcohol (C34). One of skill in the art will appreciate that other fatty alcohols are useful in the present invention.

A perfluorinated moiety can be any alkyl, alkenyl, cycloalkyl, aryl, or other group, where all the hydrogen atoms are replaced with fluorine atoms. Representative perfluorinated groups include perfluoro-$C_{1-24}$ alkyl, perfluoro-$C_{2-24}$ alkenyl, perfluoro-$C_{3-18}$ cycloalkyl, and perfluoro-$C_{6-24}$ aryl. For example, perfluoro-$C_{1-24}$ alkyl can be perfluoro-$C_{3-18}$ alkyl, perfluoro-$C_{6-10}$ alkyl, or perfluorinated methyl, ethyl, propyl, isopropyl, butyl, isobutyl, sec-butyl, tert-butyl, pentyl, isopentyl, hexyl, heptyl, octyl, nonyl, or perfluorinated decyl.

Examples of perfluoro-$C_{2-24}$ alkenyl, include perfluoro-$C_{3-18}$ alkenyl, perfluoro-$C_{6-10}$ alkenyl, or perfluorinated ethylene, propylene, 1-butenyl, 2-butenyl, iso-butene, 1-pentenyl, 2-pentenyl, 2-methyl-1-butene, 3-methyl-1-butene, 1-hexenyl, 2-hexenyl, 3-hexenyl, and isomers thereof, octenyl and isomers thereof, nonenyl and isomers thereof, or perfluorinated decenyl and isomers thereof. The perfluoro-$C_{2-24}$ alkenyl moiety can include multiple double bonds, for example perfluorinated 1,3-butadiene and 1,3,5-hexatriene. The perfluoro-$C_{2-24}$ alkenyl moiety can include cis and trans isomers in any combination, for example cis-2-butene, trans-2-butene, and cis, trans-2,4-hexadiene.

A perfluoro-$C_{3-18}$ cycloalkyl can be any cyclic or polycyclic group where all hydrogen atoms are replaced by fluorine atoms. Representative perfluorinated groups include perfluoro-$C_{3-10}$ cycloalkyl, perfluoro-$C_{5-8}$ cycloalkyl, perfluoro-$C_{i1-15}$ cycloalkyl, and perfluoro-$C_{16-18}$ cycloalkyl. Examples of perfluoro-$C_{3-18}$ cycloalkyl groups include perfluoro-cyclopropane, cyclobutane, cyclopentane, cyclohexane, cycloheptane, cyclooctane, cyclononane, and perfluoro-cyclodecane. Examples of polycyclic perfluoro-$C_{3-18}$ cycloalkyl groups include perfluoro-bicyclo[2.2.0]hexane, and bicyclo[4.4.0]decane (decalin). Perfluorinated tricyclic and higher-order cyclic variations (i.e. tetra, penta) are also useful hydrophobic groups in the present invention, as is readily envisaged by one of ordinary skill in the art.

A perfluoro-$C_{6-24}$ aryl can be any cyclic or polycyclic aryl group where all hydrogen atoms are replaced by fluorine atoms. Examples of perfluoro-$C_{6-24}$ aryl include perfluoro-$C_6$ aryl, $C_8$ aryl, $C_{10}$ aryl, $C_{12}$ aryl, $C_{14}$ aryl, $C_{16}$ aryl, $C_{18}$ aryl, $C_{20}$ aryl, $C_{20}$ aryl, $C_{22}$ aryl, and perfluoro-$C_{24}$ aryl. Each of the preceding groups can be polycyclic, including perfluorinated naphthalene ($C_{10}$ aryl), phenanthrene ($C_{14}$ aryl), anthracene ($C_{14}$ aryl), and the like. Other polycyclic variations can be readily envisaged by one of ordinary skill in the art.

In one embodiment, the hydrophobic moiety can be a lipid or a perfluorinated moiety. In one embodiment, the hydrophobic moiety can be a perfluorinated $C_{3-18}$ alkyl, —CH(perfluorinated $C_{3-18}$ alkyl)$_2$, perfluorinated $C_{3-18}$ alkenyl, perfluorinated $C_{3-8}$ cycloalkyl, or perfluorinated aryl. In one embodiment, the hydrophobic moiety can be a perfluorinated $C_{6-18}$ alkyl. In one embodiment, the hydrophobic moiety can be a perfluorinated n-hexyl or a perfluorinated n-octyl.

As discussed above, in addition to perfluorinated hydrophobic moieties, the hydrophobic moiety can also be a non-fluorous hydrophobic group such as, for example, a fatty acid, a fatty acid alcohol, or a fatty acid ester. The hydrophobic moiety can be saturated or unsaturated. In one embodiment, the hydrophobic moiety can be a $C_{6-24}$ alkyl, a $C_{8-24}$ alkenyl, a fatty acid, a sphingosine, or a ceramide.

The hydrophobic moiety can be connected to the acceptor sugar by a linker. The linker can comprise polyethylene glycol, or other polar groups such as amides, esters, ureas, and combinations of polyethylene glycol and other polar groups. The linker can also comprise short alkylene chains of up to 8 carbon atoms in length. In one embodiment, the linker is selected from the group consisting of $C_{1-6}$ alkylene- NH—C(O)—C$_{1-6}$ alkylene, and C$_{1-6}$ alkylene-NH—C(O)—(CH$_2$—(CH$_2$CH$_2$O)$_p$—NH—C(O))$_m$—C$_{1-6}$ alkylene, wherein subscript m is 0 or 1, and subscript p is an integer from 1 to 6. In one embodiment, the linker can be C$_{1-6}$ alkylene-NH—C(O)—(CH$_2$—(CH$_2$CH$_2$O)$_p$—NH—C(O))$_m$—C$_{1-6}$ alkylene, subscript m is 1, and subscript p is 3. In one embodiment, the linker can be C$_{1-6}$ alkylene-NH—C(O)—(CH$_2$—(CH$_2$CH$_2$O)$_p$—NH—C(O))$_m$-C$_{1-6}$ alkylene, subscript m is 1, and subscript p is 6.

In one embodiment, the acceptor sugar has the structure:

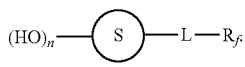

S represents a monosaccharide, disaccharide or oligosaccharide. L represents a linker that can be C$_{1-6}$ alkylene-NH—C(O)—C$_{1-6}$ alkylene, or C$_{1-6}$ alkylene-NH—C(O)—(CH$_2$—(CH$_2$CH$_2$O)$_p$—NH—C(O))$_m$—C$_{1-6}$ alkylene, where subscript m is 0 or 1, and subscript p is an integer from 1 to 6. $R_f$ represents a hydrophobic moiety that can be perfluorinated C$_{3-18}$ alkyl, —CH(perfluorinated C$_{3-18}$ alkyl)$_2$, perfluorinated C$_{3-18}$ alkenyl, perfluorinated C$_{3-8}$ cycloalkyl, and perfluorinated aryl. Finally, (HO)$_n$ represents the free hydroxyl groups on the sugar S, and subscript n is an integer from 3 to 20.

Sugar S can be a monosaccharide, disaccharide, or oligosaccharide. A monosaccharide can be any sugar or its derivative. Examples of monosaccharides include, but are not limited to, dioses such as glycoaldehyde; trioses such as D and L-glyceraldehyde; tetroses such as D and L-erythrose, threose, and erythrulose; pentoses such as D and L-arabinose, lyxose, ribose, xylose, ribulose, and xylulose; hexoses such as D and L-allose, altrose, glucose, mannose, gulose, idose, galactose, fructose, and talose; aminosugars such as N-acetylglucosamine, galactosamine, glucosamine, sialic acid, and D and L-duanosamine; and sulfosugars such as sulfoquinovose. Deuterated, oxidized, and N-acetyl derivatives of the foregoing are also suitable sugars. Oxidized derivatives can be carboxylic acid derivatives of the respective sugar at any carbon in the sugar capable of being oxidized to a carboxylic acid in the sugar.

Disaccharides are two monosaccharides linked together by glycosidic bonds. The glycosidic bonds can be O-, N-, or S-glycosidic bonds, and can be either α- or β-glycosidic bonds. Exemplary disaccharides include sucrose, lactose, maltose, and lactulose. However, any hydrolytically stable combination of two monosaccharides can be a suitable disaccharide. Oligosaccharides contain three or more monosaccharides linked by glycosidic bonds in the same manner as the aforementioned disaccharides.

The acceptor sugar contains a hydrophobic moiety that is connected to the sugar portion via the linker. In one embodiment, the linker L can be any of the linkers listed above. In one embodiment, the linker L can be a C$_3$ alkylene-NH—C(O)—C$_2$ alkylene.

$R_f$ can be any of the hydrophobic moieties listed above. In one embodiment, $R_f$ can be a perfluoro C$_{6-10}$ alkyl. In one embodiment, $R_f$ can be C$_6$F$_{13}$. In one embodiment, $R_f$ can be C$_8$F$_{17}$.

In one embodiment, the acceptor sugar has the structure:

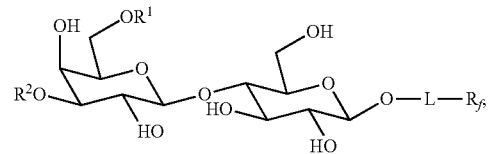

where R$^1$ and R$^2$ are each H and L and R$_f$ can be any of the respective groups set forth above.

In one embodiment, the isolated oligosaccharide can have the structure:

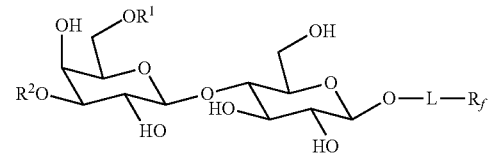

wherein R$^1$ and R$^2$ can independently be hydrogen, Fucα1-2, GlcNAcβ1-3, (Galβ1-4GlcNAc)$_{1-5}$β1-3, (Galβ1-3GlcNAc)$_{1-5}$β1-3, Galα1-3, Galα1-4, GalNAcβ1-4, Galβ1-3GalNAcβ1-4, Siaα2-3Galα1-3GalNAcβ1-4, Siaα2-3, Siaα2-8Siaα2-3, Siaα2-8Siaα2-8Siaα2-3, or Siaα2-6, such that at least one of R$^1$ and R$^2$ is other than hydrogen.

The method of the present invention uses a glycotransferase as part of the preparation of an oligosaccharide or glycolipid. In one embodiment, more than one glycotransferase can be used at the same time. There is no limit to the number of different glycotransferases that can be used simultaneously, provided that sufficient quantities of the desired oligosaccharide can be obtained. In one embodiment, the glycosyltransferase can be sialyltransferase, ucosyltransferase, mannosyltransferase, galactosyltransferase, glucosyltransferase, N-acetylgalactosaminyltransferase, N-acetylglucosyltransferase, glucuronyltransferase, or xylosyltransferase. In one embodiment, the glycotransferase can be a mixture of any of the foregoing glycotransferases. In one embodiment, up to ten different glycotransferases can be used simultaneously in one pot.

In one embodiment, the glycosyltransferase can be PmST1 E271F/R313Y, Pd2-6ST, α1-3GalT, PmST1 M144D, PmST1, PmST2, PmST3, Pd2-6ST, Psp2-6ST, Cst-I, Cst-II, α2-3SiaT, α2-6SiaT, α2-8SiaT, α2-9SiaT, α1-2FucT, α1-3FucT, α1-4FucT, α1-6FucT, α1-2ManT, α1-3ManT, α1-4ManT, α1-6ManT, β1-2ManT, β1-4ManT, α1-2GalT, α1-3GalT, α1-4GalT, α1-6GalT, β1-2GalT, β1-3GalT, β1-4GalT, α1-2GlcT, α1-3GlcT, α1-4GlcT, α1-6GlcT, β1-2GlcT, β1-3GlcT, β1-4GlcT, β1-6GlcT, α1-3GalNAcT, β1-4GalNAcT, α1-4GalNAcT, β1-3GalNAcT, α1-2GlcNAcT, α1-3GlcNAcT, α1-4GlcNAcT, α1-6GlcNAcT, β1-2GlcNAcT, β1-3GlcNAcT, β1-4GlcNAcT, β1-6GlcNAcT, β1-3GlcAT, β1-4GlcAT, α1-3Xyl, α1-6Xyl, or β1-2Xyl.

The sugar donors of the present invention can react with an acceptor sugar bearing hydrophobic moieties and a linker in the presence of a glycotransferase. Any of the sugars disclosed above as suitable for use as an acceptor sugar can also be a sugar donor.

In one embodiment, the sugar donor can be Gal (galactose), Neu5A (neuraminic acid), GlcNAc (N-acetylglucosamine), GalNAc (N-acetylgalactosamine), Fuc (fucose), GlcA (glucoronic acid), GalA (galacturonic acid) or Neu5Ac (N-acetylneuraminic acid). In one embodiment, the sugar donor can be group Galα1-3, Neu5Acα2-3, or Neu5Acα2-6.

The sugar donor can also be a nucleoside or a nucleoside phosphate, including nucleoside monophosphates, nucleoside diphosphates, and nucleoside triphosphates. The nucleoside can comprise ribonucleosides such as adenosine, guanosine, uridine, cytidine, and thymidine. The nucleoside can also comprise deoxyribonucleosides such as deoxyadenosine, deoxyguanosine, deoxyuridine, deoxycytidine, deoxythymidine, and deoxycytidine.

In one embodiment, the sugar donor can be cytidine 5'-monophosphate(CMP)-sialic acid, a guanosine 5'-diphosphate(GDP)-fucose, guanosine 5'-diphosphate(GDP)-mannose, uridine 5'-diphosphate(UDP)-galactose, uridine 5'-diphosphate(UDP)-glucose, uridine 5'-diphosphate (UDP)-N-acetylgalactosamine, a uridine 5'-diphosphate (UDP)-N-acetylglucosamine, uridine 5'-diphosphate(UDP)-glucuronic acid, and uridine 5'-diphosphate(UDP)-xylose. Any of the foregoing sugar donors can be formed in one pot.

One of skill in the art can readily synthesize any of the aforementioned sugar donors according to known methods. For example, the foregoing sugar donors can be synthesized as described below.

Cytidine 5'-monophosphate N-acetylneuraminic acid (CMP-Neu5Ac) or a CMP-Neu5Ac analog can be obtained by forming a reaction mixture comprising a CMP-sialic acid synthetase, cytidine triphosphate, and N-acetylneuraminic acid (Neu5Ac) or a Neu5Ac analog to form a CMP-Neu5Ac or CMP-Neu5Ac analog. The CMP-Neu5Ac or CMP-Neu5Ac analog can comprise an α2-3-, α2-6, α2-8, or α2-9-linked sialic acid residue.

The Neu5Ac or Neu5Ac analog can be obtained by forming a reaction mixture comprising a sialic acid aldolase, pyruvic acid or derivatives thereof, and N-acetylmannosamine or derivatives thereof. The Neu5Ac or Neu5Ac analog can be formed in one pot.

Guanosine 5'-diphosphate fucose (GDP-Fuc) or a GDP-Fuc analog can be obtained by forming a reaction mixture comprising a bifunctional L-fucokinase and GDP-Fuc pyrophosphorylase, optionally with an inorganic pyrophosphatase, adenosine triphosphate (ATP), guanosine triphosphate (GTP), L-fucose or a fucose analog to form a GDP-Fuc or GDP-Fuc analog. The GDP-Fuc or GDP-Fuc analog can comprise an α1-2-, α1-3, α1-4, or α1-6-linked fucose residue.

Guanosine 5'-diphosphate(GDP)-mannose (GDP-Man) or GDP-Man analog can be obtained by forming a reaction mixture comprising a GDP-Man pyrophosphorylase, with or without an inorganic pyrophosphatase, guanosine triphosphate (GTP), and Man-1-phosphate (Man-1-P) or a Man-1-P analog to form a GDP-Man or GDP-Man analog. The GDP-Man or GDP-Man analog can comprise an α1-2, α1-3, α1-4-, α1-6-, β1-2, or β1-4-linked mannose residue.

The Man-1-P or Man-1-P analog can be obtained by forming a reaction mixture comprising a mannose-1-phosphate kinase, adenosine triphosphate (ATP). The Man-1-P or Man-1-P analog can be obtained in one pot.

Uridine 5'-diphosphate(UDP)-galactose (UDP-Gal) or a UDP-Gal analog can be obtained by forming a reaction mixture comprising a UDP-Gal pyrophosphorylase, with or without an inorganic pyrophosphatase, uridine triphosphate (UTP), and Gal-1-phosphate (Gal-1-P) or a Gal-1-P analog. The UDP-Gal or UDP-Gal analog can comprise an α1-2-, α1-3-, α1-4, α1-6, β1-2, β1-3, or β1-4-linked galactose residue.

The Gal-1-P or a Gal-1-P analog can be obtained by forming a reaction mixture comprising a galactokinase, adenosine triphosphate (ATP), and galactose or derivatives thereof. The Gal-1-P or Gal-1-P analog can be formed in one pot.

Uridine 5'-diphosphate(UDP)-glucose (UDP-Glc) or a UDP-Glc analog can be obtained by forming a reaction mixture comprising a UDP-Glc pyrophosphorylase, optionally with an inorganic pyrophosphatase, uridine triphosphate (UTP), and Glc-1-phosphate (Glc-1-P) or a Glc-1-P. The UDP-Glc or a UDP-Glc analog can comprise an α1-2, α1-3, α1-4-, α1-6-, β1-2, β1-3, β1-4 or β1-6-linked glucose residue.

The Glc-1-P or Glc-1-P analog can be obtained by forming a reaction mixture comprising a monosaccharide-1-phosphate kinase, adenosine triphosphate (ATP), and glucose or derivatives thereof. The Glc-1-P or Glc-1-P analog can be formed in one pot.

Uridine 5'-diphosphate(UDP)-N-acetylgalactosamine (UDP-GalNAc) or a UDP-GalNAc analog can be obtained by forming a reaction mixture comprising a UDP-Gal1NAc pyrophosphorylase, optionally with an inorganic pyrophosphatase, uridine triphosphate (UTP), and GalNAc-1-phosphate (GalNAc-1-P) or a GalNAc-1-P analog. UDP-GalNAc or UDP-GalNAc analog can comprise an α1-3, α1-4-, β1-3, or β1-4-linked glucose residue.

The GalNAc-1-P or GalNAc-1-P analog can be obtained by forming a reaction mixture comprising an N-hexosamine-1-phosphate kinase, adenosine triphosphate (ATP), and GalNAc or derivatives thereof to form. The GalNAc-1-P or GalNAc-1-P analog can be formed in one pot.

Uridine 5'-diphosphate(UDP)-N-acetylglucosamine (UDP-GlcNAc) or a UDP-GlcNAc analog can be obtained by forming a reaction mixture comprising a UDP-GlcNAc pyrophosphorylase, with or without an inorganic pyrophosphatase, uridine triphosphate (UTP), and GlcNAc-1-phosphate (GlcNAc-1-P) or a GlcNAc-1-P analog. The UDP-GlcNAc or UDP-GlcNAc analog can comprise an α1-2, α1-3, α1-4-, α1-6-, β1-2, β1-3, β1-4, or β1-6-linked GlcNAc residue.

The GlcNAc-1-P or GlcNAc-1-P analog can be obtained by forming a reaction mixture comprising a hexosamine-1-phosphate kinase, adenosine triphosphate (ATP), and GlcNAc or derivatives thereof to form. The GlcNAc-1-P or GlcNAc-1-P can be formed in one pot.

Uridine 5'-diphosphate(UDP)-glucuronic acid (UDP-GlcA) or a UDP-GlcA analog can be obtained by forming a reaction mixture comprising a UDP-GlcA pyrophosphorylase, with or without an inorganic pyrophosphatase, uridine triphosphate (UTP), and GlcA-1-phosphate (GlcA-1-P) or a GlcA-1-P analog. The UDP-GlcA or UDP-GlcA analog can comprise an β1-3, or β1-4-linked G1cA residue.

The GlcA-1-P or GlcA-1-P analog can be obtained by forming a reaction mixture comprising a hexosamine-1-phosphate kinase, adenosine triphosphate (ATP), and GlcA or derivatives thereof. The GlcA-1-P or GlcA-1-P analog can be formed in one pot.

UDP-xylose (UDP-Xyl) or a UDP-Xyl analog can be obtained by forming a reaction mixture comprising a UDP-Xyl pyrophosphorylase, with or without an inorganic pyrophosphatase, uridine triphosphate (UTP), and Xyl-1-phosphate (Xyl-1-P) or a Xyl-1-P analog. The UDP-Xyl or UDP-Xyl analog can comprise an α1-3, α1-6, or β1-2-linked xylose residue.

The Xyl-1-P or Xyl-1-P analog can be obtained by forming a reaction mixture comprising a xylose-1-phosphate kinase, adenosine triphosphate (ATP), and Xyl or derivatives thereof.

The solid-phase extraction (SPE) cartridge can be part of any solid phase chromatography system capable of separating perfluorinated or hydrophobic compounds. The stationary phase in the SPE cartridge suitable for isolating the oligosaccharides and glycolipids of the present invention typically comprises silica particles chemically modified with hydrophobic alkyl or aryl functional groups (for oligosaccharides containing non-fluorous hydrophobic moieties) or SPE cartridges such as FluoroFlash® (for oligosaccharides containing perfluoro hydrophobic moieties), both available from SigmaAldrich.

One of skill in the art can appreciate that the choice of a particular SPE cartridge is not important so long as the oligosaccharides of the present invention can be isolated. The mobile phase used for isolating the oligosaccharide or glycolipid can be any solvent system, including mixed solvent systems, capable of effecting the separation. Suitable solvents for isolating the oligosaccharide or glycolipid include alcohols such as methanol.

In one embodiment, the solid-phase extraction cartridge is selected from the group consisting of a fluorous SPE cartridge and a C18 SPE cartridge.

In one embodiment, the isolated oligosaccharide is prepared in a yield of at least 50%. In one embodiment, the isolated oligosaccharide is prepared in a yield of at least 65%. In one embodiment, the isolated oligosaccharide is prepared in a yield of at least 75%. In one embodiment, the isolated oligosaccharide is prepared in a yield of at least 85%. In one embodiment, the isolated oligosaccharide is prepared in a yield of at least 90%.

In one embodiment, the isolated oligosaccharide is selected from the group consisting of: a) $R^1$ is hydrogen and $R^2$ is Neu5Acα2-3, b) $R^1$ is Neu5Acα2-6 and $R^2$ is hydrogen, and c) $R^1$ is hydrogen and $R^2$ is Galα1-3.

IV. Examples

All chemicals were purchased from commercial suppliers and used without further purification Anhydrous solvents were used to carry out organic reactions under inert argon or nitrogen environment. $^1$H NMR and $^{13}$C NMR spectra were recorded on a Varian Inova-600 spectrometer or a Bruker Avance-800 spectrometer. $^{19}$F NMR spectra were recorded on a Varian Mercury-300 spectrometer. MALDI-TOF analysis of samples was carried out using an Applied Biosystems 4700 MALDI TOF/TOF with each reaction mixture (0.5 μL) diluted 100 fold using a solvent mixture ($H_2O$:MeOH:TFA=50:50:0.1, by volume). The diluted reaction mixture (0.5 μL) was mixed with the same volume of 2,5-dihydroxybenzoic acid solution (10 mg/mL in 50% of acetonitrile in water) on a well spot of a stainless steel plate (ABI 01-192-6-AB). The glycans were analyzed in the positive ion reflector mode with a 355 nm (200 Hz) Nd:YAG laser. The instrument was calibrated with ABI peptide standards (4700 Mass standards kit, 4333604). Spectra were analyzed using the GPS Explorer software (v. 3.0) (Applied Biosystems). High resolution electrospray ionization (HR-ESI) mass spectra were obtained using Thermo Electron LTQ-Orbitrap Hybrid MS at the Mass Spectrometry Facility in the University of California, Davis. Silica gel 60 Å(200-425 mesh, Fisher Chemical) was used for flash column chromatography. Thin-layer chromatography (TLC) was performed on silica gel plates 60 GF254 (Sorbent technologies) using p-anisaldehyde sugar stain or 5% sulfuric acid in ethanol stain for detection.

Disaccharide Acceptor Sugars With Various Linkers and Hydrophobic Moieties

A series of acceptor sugars comprising various linkers and perfluorinated hydrophobic moieties was synthesized. Lactose was chosen as the sugar component (S) because it is a common core structure in many glycans and a suitable acceptor for numerous glycosyltransferases. Examples 1-4 and 6 detail the synthesis of acceptor sugars 1-8 containing various linkers and different lengths of perfluoroalkanes including $C_8F_{17}$, $C_6F_{13}$, and $C_3F_7$ (Scheme 1). Examples 1-4 outline the synthesis of acceptor sugars 1-4 according to Scheme 1, Example 5 details the general procedure for attaching a polyethylene glycol linker to lactosides, and Example 6 discloses the synthesis of acceptor sugars 5-8 according to Scheme 1.

Scheme 1. Selected synthesized acceptor sugars bearing fluorous hydrophobic moieties.

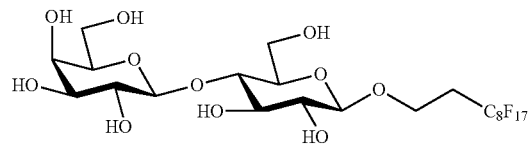

1

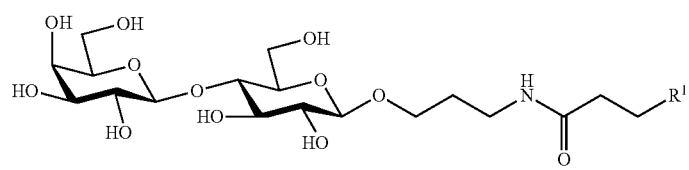

2 $R^1 = C_8F_{17}$
3 $R^1 = C_6F_{13}$
4 $R^1 = C_3F_7$

-continued

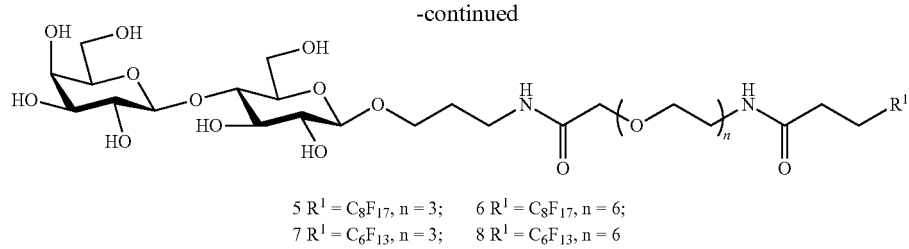

5 $R^1 = C_8F_{17}$, n = 3;  6 $R^1 = C_8F_{17}$, n = 6;
7 $R^1 = C_6F_{13}$, n = 3;  8 $R^1 = C_6F_{13}$, n = 6

Lactoside 1, tagged with $C_8F_{17}$, was synthesized for comparative purposes by direct chemical glycosylation (Scheme 1) and tested as an acceptor substrate for *Pasteurella multocida* α2-3-sialyltransferase 1 E271F/R313Y mutant (PmST1 E271F/R313Y) with decreased α2-3-sialidase activity. Examples 15-17 describe exemplary one pot multienzyme glycosylation reactions according to the present invention.

Scheme 2. Test of $C_8F_{17}$-tagged acceptor sugar 1 as the glycosyltransferase acceptor in a one-pot two-enzyme sialylation system containing NmCSS and PmST1 E271F/R313Y.

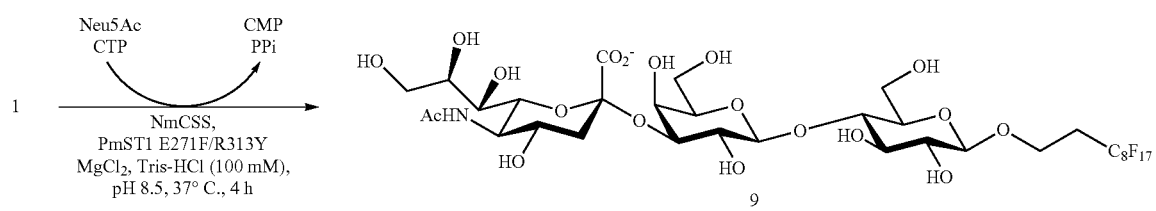

To test the suitability of lactoside 1 as an acceptor sugar, a one-pot two-enzyme system containing PmST1 E271F/R313Y and *Neisseria meningitidis* CMP-sialic acid synthetase (NmCSS) (Scheme 2) was used. The reaction was inefficient and only a trace amount (<10%) of sialylated product was detected, as shown by thin-layer chromatography (TLC) and matrix-assisted laser desorption/ionization-time of flight (MALDI-TOF) mass spectrometry.

The low water solubility of lactoside 1 was believed to contribute significantly to the low efficiency of the reaction. Furthermore, the rigid and rod-like perfluorooctyl chain close to the lactoside may also prevent compound 1 from being a good acceptor for PmST1 E271F/R313Y. Adding an organic solvents such as DMF, DMSO, methanol, or acetonitrile in amounts up to 30% v/v, or 0.1% of detergents such as Triton X-100, Tween 80, or HFE-7200 did not improve the yield.

Scheme 3. OPME glycosylation of lactioside acceptor sugars being fluorous hydrophobic moieties.

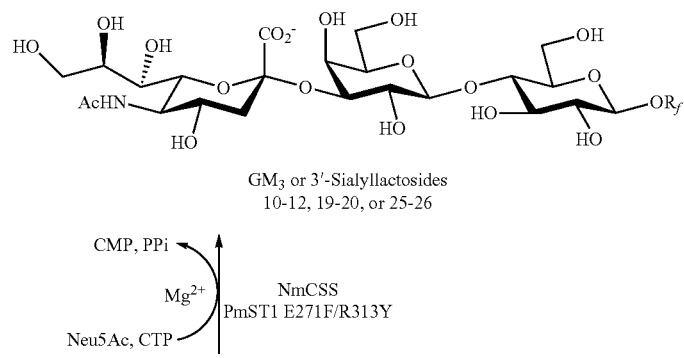

GM₃ or 3'-Sialyllactosides
10-12, 19-20, or 25-26

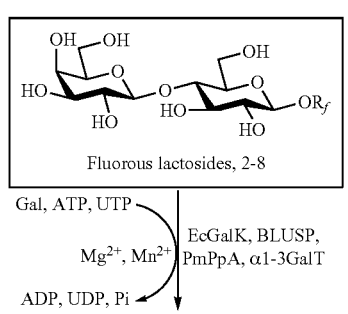

Fluorous lactosides, 2-8

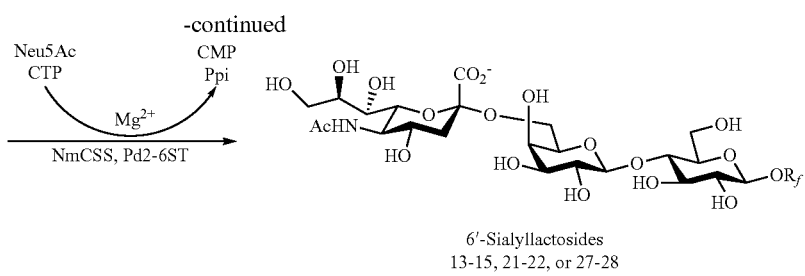

6′-Sialyllactosides
13-15, 21-22, or 27-28

Gal, ATP, UTP → EcGalK, BLUSP, PmPpA, α1-3GalT
$Mg^{2+}, Mn^{2+}$
ADP, UDP, Pi

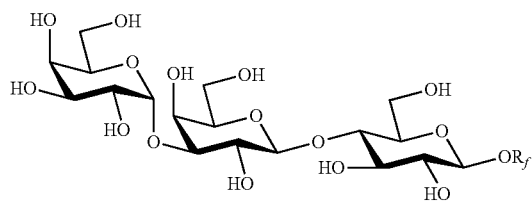

iGb$_3$ or α-Gal trisaccharides
16-18, 23-24, 29-30

$R_f$ = hydrophobic moiety

TABLE 1

OPME sialylation (pH 8.5) and galactosylation (pH 7.0) of lactosides (2-4) containing various lengths of fluorous tags.

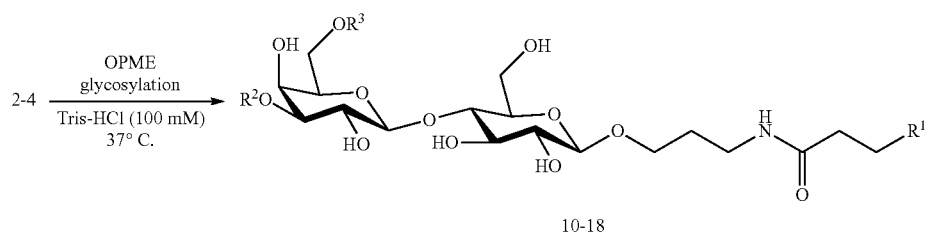

| Entry | Acceptor | R$^1$ | Enzyme | R$^2$ | R$^3$ | Product | Conversion (%)[a] |
|---|---|---|---|---|---|---|---|
| a | 2 | C$_8$F$_{17}$ | PmST1 E271F/R313Y | Neu5Acα2-3 | H | 10 | 22 ± 12[b] |
| b | 3 | C$_6$F$_{13}$ | PmST1 E271F/R313Y | Neu5Acα2-3 | H | 11 | 92 ± 5.5[b] |
| c | 4 | C$_3$F$_7$ | PmST1 E271F/R313Y | Neu5Acα2-3 | H | 12 | 89 ± 9.8[b] |
| d | 2 | C$_8$F$_{17}$ | Pd2-6ST | H | Neu5Acα2-6 | 13 | 31 ± 18[b] |
| e | 3 | C$_6$F$_{13}$ | Pd2-6ST | H | Neu5Acα2-6 | 14 | 94 ± 6.0[b] |
| f | 4 | C$_3$F$_7$ | Pd2-6ST | H | Neu5Acα2-6 | 15 | qt.[b] |
| g | 2 | C$_8$F$_{17}$ | α1-3GalT | Galα1-3 | H | 16 | 10 ± 0.0[c] |
| h | 3 | C$_6$F$_{13}$ | α1-3GalT | Galα1-3 | H | 17 | 60 ± 0.5[c] |
| i | 4 | C$_3$F$_7$ | α1-3GalT | Galα1-3 | H | 18 | qt.[c] |

[a]Determined by thin-layer chromatography and ImageQuant 5.2 after staining of the plate. Reaction was assayed at 4 h[b] or 15 h[c]. Abbreviation qt. is quantitative yield.

TABLE 2

OPME sialylation glycosylation (pH 8.5) and galactosylation (pH 7.0) of acceptor sugar lactosides (5-8) bearing fluorous hydrophobic moieties and containing a TEG or an HEG linker.

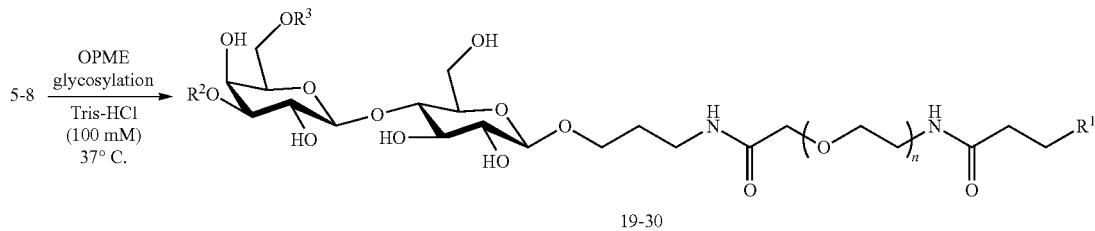

19-30

| Entry | Acceptor | $R^1$ | n | Enzyme | $R^2$ | $R^3$ | Product | Conversion (%)[a] |
|---|---|---|---|---|---|---|---|---|
| j | 5 | $C_8F_{17}$ | 3 | PmST1 E271F/R313Y | Neu5Acα2-3 | H | 19 | 65 ± 11[b] |
| k | 6 | $C_8F_{17}$ | 6 | PmST1 E271F/R313Y | Neu5Acα2-3 | H | 20 | 55 ± 7.8[b] |
| l | 5 | $C_8F_{17}$ | 3 | Pd2-6ST | H | Neu5Acα2-6 | 21 | 47 ± 10[b] |
| m | 6 | $C_8F_{17}$ | 6 | Pd2-6ST | H | Neu5Acα2-6 | 22 | 52 ± 5.6[b] |
| n | 5 | $C_8F_{17}$ | 3 | α1-3GalT | Galα1-3 | H | 23 | 81 ± 8.0[c] |
| o | 6 | $C_8F_{17}$ | 6 | α1-3GalT | Galα1-3 | H | 24 | 66 ± 1.0[c] |
| p | 7 | $C_6F_{13}$ | 3 | PmST1 E271F/R313Y | Neu5Acα2-3 | H | 25 | 70 ± 4.8[b] |
| q | 8 | $C_6F_{13}$ | 6 | PmST1 E271F/R313Y | Neu5Acα2-3 | H | 26 | 80 ± 15[b] |
| r | 7 | $C_6F_{13}$ | 3 | Pd2-6ST | H | Neu5Acα2-6 | 27 | 65 ± 7.9[b] |
| s | 8 | $C_6F_{13}$ | 6 | Pd2-6ST | H | Neu5Acα2-6 | 28 | 66 ± 25[b] |
| t | 7 | $C_6F_{13}$ | 3 | α1-3GalT | Galα1-3 | H | 29 | 71 ± 0.5[c] |
| u | 8 | $C_6F_{13}$ | 6 | α1-3GalT | Galα1-3 | H | 30 | 69 ± 1.0[c] |

[a]Determined by thin-layer chromatography and ImageQuant 5.2 software after staining. Reaction was assayed at 4 h[b] or 15 h[c]. Abbreviation qt. is quantitative yield.

To increase the solubility of the fluorous-tagged lactosides and to examine how the length of the fluorous tags affects the efficiency of the enzymatic reactions, fluorous-tagged lactosides (2-4) (Scheme 1) containing a propylamide linker and different lengths of fluoroalkyl chains were synthesized and used as the acceptor sugars in a one-pot two-enzyme system containing NmCSS and PmST1 E271F/R313Y (Scheme 3). Sialosides (10-12) were obtained with varied yields of 22%, 92%, and 89% from lactosides tagged with $C_8F_{17}$, $C_6F_{13}$, and $C_3F_7$, respectively (entries a-c for products 10-12) (Table 1).

These results indicated that the decrease of the fluorous tag length led to increase of the enzyme activity. In comparison, $C_8F_{17}$- and $C_6F_{13}$-tagged sialosides 10 and 11 were easily purified by a FSPE cartridge. Similar effects of the fluorous tag lengths on the glycosylation yields and FSPE product purification were observed for a one-pot two-enzyme α2-6-sialylation system containing NmCSS and *Photobacterium damselae* α2-6-sialyltransferase (Pd2,6ST) (Table 1, entries d-f for products 13-15) and a one-pot four-enzyme galactosylation system containing *Escherichia coli* galactokinase (EcGalK), *Bifidobacterium longum* UDP-sugar pyrophosphorylase (BLUSP), *Pasteurella multocida* inorganic pyrophosphatase (PmPpA), and bovine α1-3-galactosyltransferase (α1-3GalT) (Table 1, entries g-i for products 16-18).

In order to improve the compatibility of lactosides with longer hydrophobic moieties (e.g. $C_8F_{17}$) to the OPME glycosylation reactions, a tri-ethylene glycol (TEG) or a hexa-ethylene glycol (HEG) linker was introduced to obtain fluorous-tagged lactosides 5-8 (Scheme 1). OPME α2-3/6-sialylation, and α1-3-galactosylation reactions (Scheme 3) showed that the TEG and HEG linkers significantly improved the yields of $C_8F_{17}$-tagged lactosides (Table 2).

The length of the oligo(ethylene glycol) (OEG) linker with either 3 or 6 ethylene glycol repeats, however, did not affect the efficiency of the OPME reactions significantly (Table 2). While TEG/HEG-$C_6F_{13}$-tagged lactosides still led to better yields, TEG/HEG-$C_8F_{17}$-tagged lactosides provided sufficiently good yields for practical production of glycosylated products.

Preparative-scale synthesis and FSPE cartridge purification of GM3, 6'-sialyllactoside, and iGb$_3$ glycan analogs (11, 14, 23, 25, 27, and 29) were carried out (Table 3 and Examples 19-24). After total consumption of the fluorous-tagged lactoside acceptor in each OPME reaction by TLC monitoring, the reaction mixture was centrifuged and the supernatant was purified using an 10 c.c. FSPE cartridge containing 2 g of fluorous silica gel by simply loading the reaction mixture to the cartridge, washing with four-column volumes of water, and eluting the fluorous-tagged product using 100% MeOH.

TABLE 3

Preparative-scale OPME synthesis of oligosaccharides with FSPE cartridge purification.

| Acceptor | Enzyme | Product | Yield (%)[a] |
|---|---|---|---|
| 3 | PmST1 E271F/R313Y | 11 | 72 |
| 3 | Pd2-6ST | 14 | 79 |
| 5 | α1-3GalT | 23 | 82[b] |
| 7 | PmST1 E271F/R313Y | 25 | 86 |
| 7 | Pd2-6ST | 27 | qt. |
| 7 | α1-3GalT | 29 | 89 |

[a]Isolated yields;
[b]The reaction mixture was purified by FSPE and underwent another round of OPME reaction.
Abbreviation qt. is quantitative yield.

Nuclear magnetic resonance (NMR) spectroscopy and high resolution mass spectrometry (HRMS) analyses demonstrated that one-step FSPE cartridge purification was sufficient to provide desired products with high purity (Supporting information). It is noteworthy that the FSPE cartridge purification is suitable for purifying both neutral (galactosides) and negatively charged (sialosides) trisaccharide products in a simple, quick, and efficient manner.

Advantageously, the purification process of the present invention takes 5-7 minutes, which is substantially faster than conventional silica gel purification (2-6 hours) and size-exclusion column chromatography (>3 hours) purification for unprotected sugars. The fast purification of fluorous-tagged glycans also improves the yield by subjecting the mixture of fluorous-tagged glycan acceptor and product for the second round of enzymatic synthesis (e.g. synthesizing compound 23 in Table 3).

Synthesis of Oligosaccharides Containing 3-10 Monosaccharides

Naturally occurring glycans typically contain from 3-10 monosaccharide building blocks. The inventive method disclosed herein can be used to synthesize oligosaccharides containing from 3-10 monosaccharides while retaining the ability to easily purify the products on FSPE cartridges.

Oligosaccharides containing from 3-10 monosaccharides were synthesized using OPME glycosylation reactions according to the methods disclosed herein (Examples 7-14). The OPME reactions included *Neisseria meningitidis* LgtA (NmLgtA, a β1-3-GlcNAc transferase), *Neisseria meningitidis* LgtB (NmLgtB, a β1-4-galatocsyltransferase) and their corresponding sugar nucleotide (UDP-sugars, e.g. UDP-GlcNAc for NmLgtA and UDP-Gal for NmLgtB).

Figure 4:
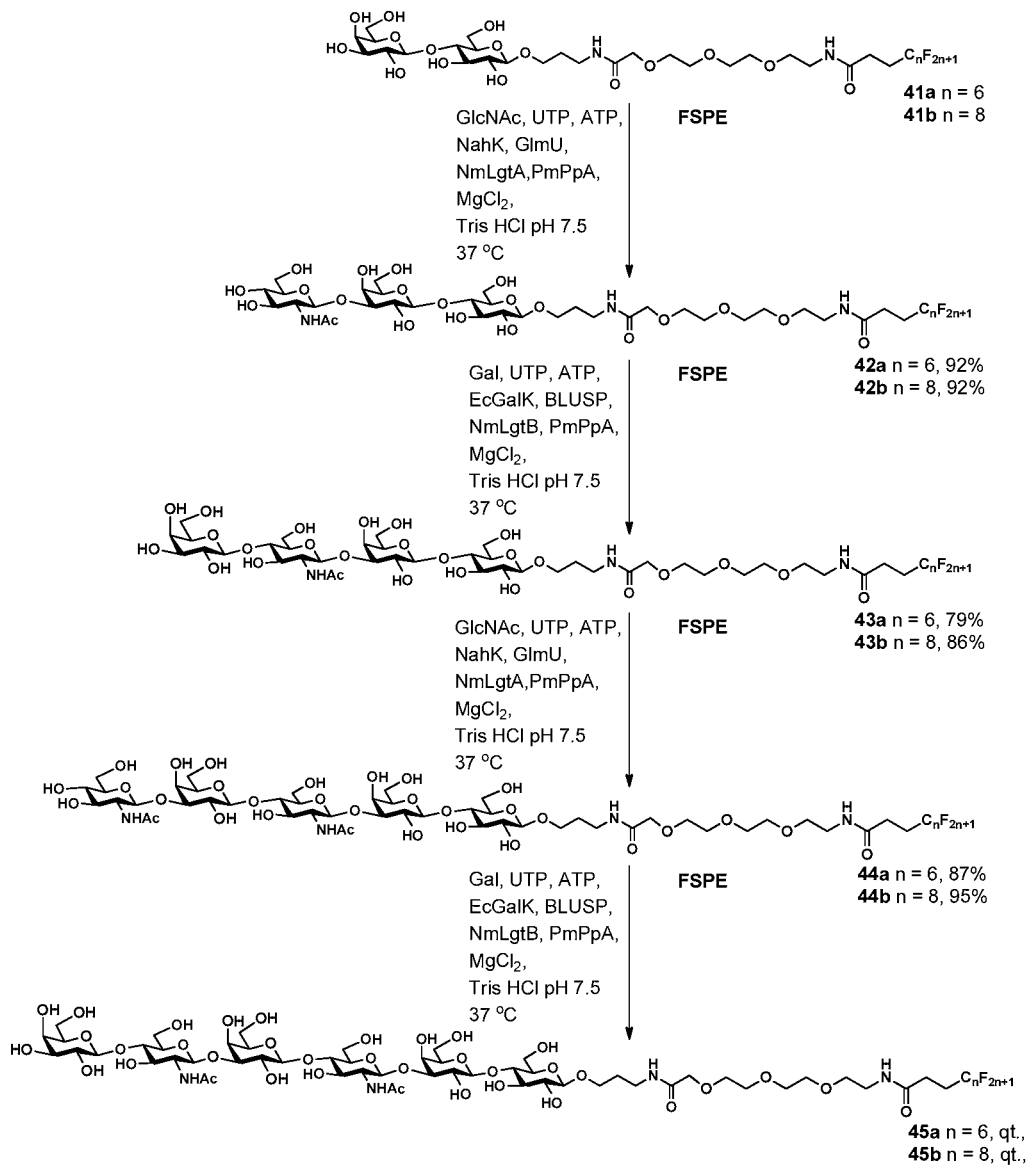
FIG. 4 shows a scheme for an exemplary sequential stepwise one-pot multienzyme (OPME) glycosylation of LacβProNH-TEG-$C_nF_{2n+1}$ (n=6 or 8) and fluorous solid-phase extraction (FSPE)-based purification of (LacNAcβ1-3)$_2$LacβProNH-TEG-$C_nF_{2n+1}$ (n=6 or 8).

In one embodiment, the fluorous-tagged glycans are built up by sequential stepwise OPME glycosylation reactions using either NmLgtA or NmLgtB with their corresponding UDP-sugar biosynthetic enzymes in each step (FIG. 4).

Figure 5:
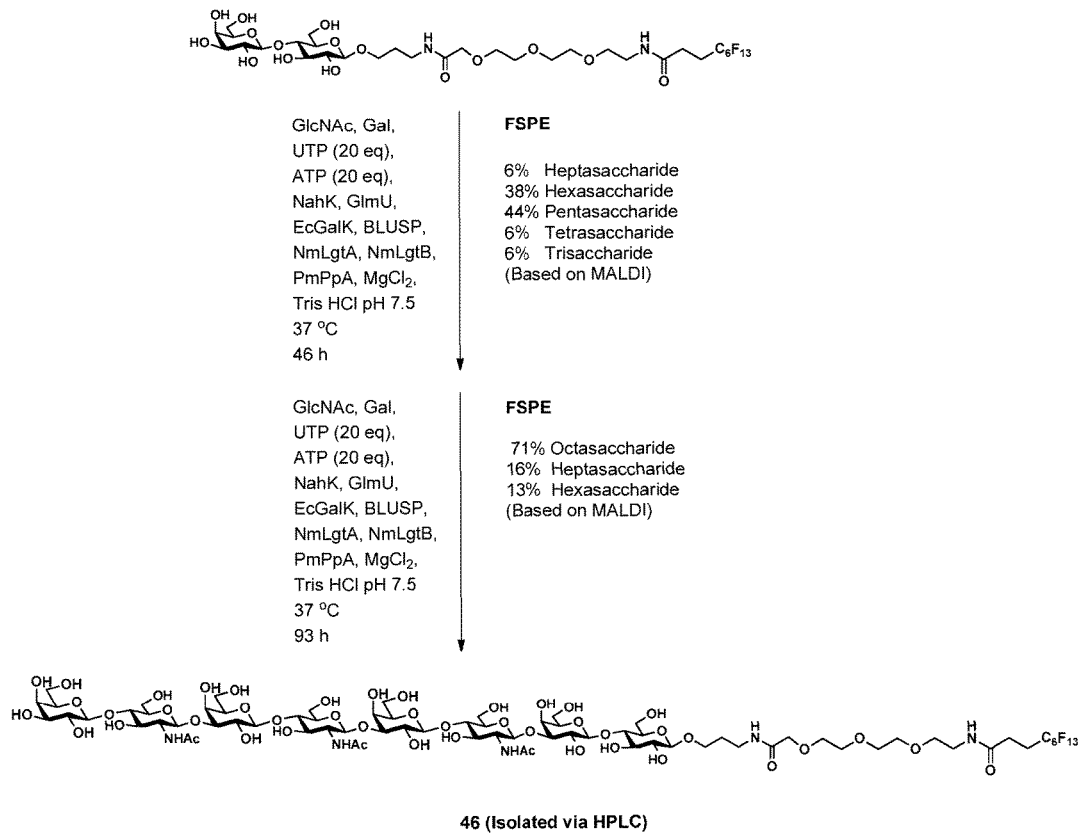
FIG. 5 shows a scheme for an exemplary one-pot seven-enzyme (OP7E) glycosylation for the synthesis of (LacNAcβ1-3)₃LacβProNH-TEG-C₆F₁₃ from LacβTEG-C₆F₁₃.

In another embodiment, a mixture of all enzymes including both NmLgtA, NmLgtB, and biosynthetic enzymes for synthesizing both UDP-GlcNAc and UDP-Gal with suitable starting materials for synthesizing longer oligosaccharides was used (FIG. 5). The oligosaccharides can be obtained by mixing the glycosyl acceptor (LacβProNH-TEG-$C_6F_{13}$) with both glycosyltransferases (NmLgtA and NmLgtB), using excess amounts (20 eq.) of GlcNAc, Gal, ATP, and UTP to synthesize a mixture of the trisaccharide, tetrasaccharide, pentasaccharide, hexasaccharide, etc. products. The reaction mixture was then loaded directly to an FSPE cartridge and washed with 100% water. The collected water washes were then analyzed via MALDI-TOF to detect if any fluorous-tagged glycans have been washed out.

The synthesis of fluorous-tagged acceptor sugars 1-4 containing short alkyl and propylamide linkers is described below.

Example 1

Synthesis of Lacβ$C_8F_{17}$ (1)

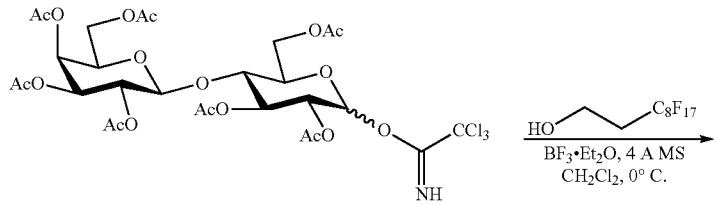

31

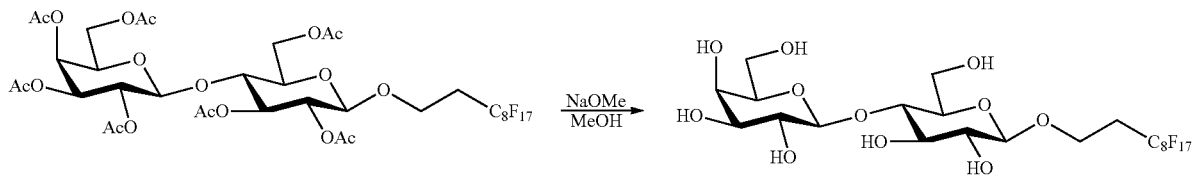

32      1

BF$_3$Et$_2$O (25 μL, 0.20 mmol) in CH$_2$Cl$_2$ (2 mL) was added drop-wise to a solution of lactosyl trichloroacetimidate 31 (123 mg, 0.158 mmol), 1H, 1H,2H,2H-perfluoro-1-decanol (46 mg, 0.1 mmol), activated 4 Å molecular sieves (400 mg), and CH$_2$Cl$_2$ (5 mL) at 0° C. The mixture was allowed to slowly warm up to room temperature and stirred for 20 h. The mixture was filtered over Celite®, concentrated, and then purified via silica gel column chromatography (EtOAc:Hexane=1:5 to 1:1 by volume) to afford peracetylated lactoside (32) as a white solid (90 mg, 82%). $^1$H NMR (600 MHz, CDCl$_3$) δ 5.34 (dd, 1H, J=1.2 Hz and 3.6 Hz), 5.19 (t, 1H, J=9.0 Hz), 5.10 (dd, 1H, J=7.8 Hz and 10.2 Hz), 4.95 (dd, 1H, J=3.0 Hz and 10.2 Hz), 4.88 (dd, 1H, J=8.4 Hz and 9.6 Hz), 4.50-4.46 (m, 3H), 4.14-4.05 (m, 4H), 3.88-3.77 (m, 3H), 3.61 (m, 1H), 2.50-2.33 (m, 2H), 2.14 (s, 3H), 2.10 (s, 3H), 2.05 (s, 3H), 2.03 (s, 6H), 2.01 (s, 3H), 1.96 (s, 3H). $^{13}$C (151 MHz, CDCl$_3$) δ 170.30, 170.27, 170.09, 170.02, 169.67, 169.56, 160.02, 105.00, 101.06, 100.60, 76.16, 72.75, 72.57, 71.31, 70.94, 70.69, 69.08, 66.56, 61.82, 60.76, 31.43, 20.75, 20.71, 20.61, 20.59 (2C), 20.48, 20.45. $^{19}$F NMR (282 MHz, CDCl$_3$) 67 =−81.18 (s, 3F, CF$_3$), −113.86 (s, 2F, CF$_2$), −122.36 (m, 6F, 3CF$_2$), −123.17 (s, 2F, CF$_2$), −124.01 (s, 2F, CF$_2$), −126.56 (s, 2F, CF$_2$).

Sodium methoxide was added to a mixture of compound 32 (294 mg, 0.27 mmol) and MeOH (30 mL) until pH~10 under room temperature. After 2 h, the mixture was neutralized with DOWEX HCR-W2 (H$^+$) resin. After filtration, the residue was concentrated and purified via FSPE to afford LacβC$_8$F$_{17}$ (1) as a white solid (156 mg, 73%). $^1$H NMR (800 MHz, CD$_3$OD) δ 4.36 (d, 1H, J=7.7 Hz), 4.35 (d, 1H, J=7.8 Hz), 4.18 (dt, 1H, J=7.0 Hz and 10.3 Hz), 3.93-3.83 (m, 3H), 3.83-3.75 (m, 2H), 3.70 (dd, 1H, J=4.6 Hz and 11.5 Hz), 3.61-3.51 (m, 4H), 3.48 (dd, 1H, J=3.3 Hz and 9.7 Hz), 3.44 (m, 1H), 3.26 (dd, 1H, J=7.9 Hz and 9.1 Hz), 2.63-2.54 (m, 2H). $^{13}$C NMR (201 MHz, CD$_3$OD) δ 105.10, 104.45, 80.46, 77.10, 76.56, 76.37, 74.82, 74.60, 72.56, 70.32, 70.30, 62.51, 61.82, 32.51 (t, J=21.2 Hz). $^{19}$F NMR (282 MHz, CD$_3$OD) δ −82.79 (s, 3F, CF$_3$), −114.90 (s, 2F, CF$_2$), −123.33 (s, 2F, CF$_2$), −124.17 (m, 6F, 3CF$_2$), −125.07 (s, 2F, CF$_2$), −127.72 (s, 2F, CF$_2$). HRMS (ESI) m/z calcd for [C$_{22}$H$_{25}$F$_{17}$O$_{11}$+H]+789.1213, found 789.1198.

Example 2

Synthesis of LacβProNH-C$_8$F$_{17}$ (2)

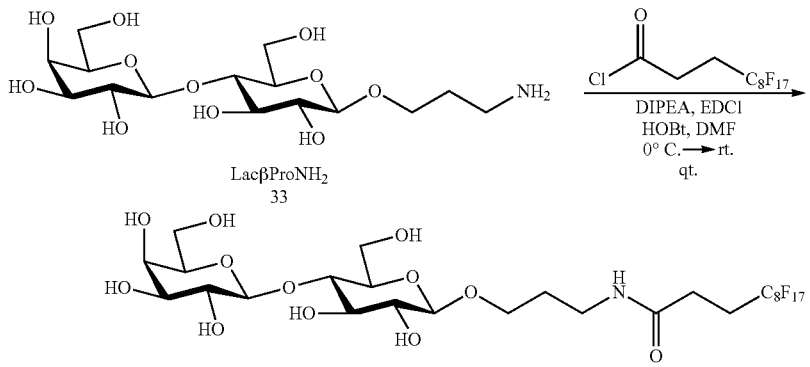

To a solution of LacβProNH$_2$ (33) (71 mg, 0.18 mmol) and 4,4,5,5,6,6,7,7,8,8,9,9,10,10,11,11-heptadecafluoroundecanoylchloride (117 mg, 0.23 mmol) in 7 mL anhydrous DMF, dry diisopropylethylamine (40 μL) was added under argon atmosphere at 0° C. The mixture was allowed to slowly warm up to room temperature and stirred for 48 h. After monitoring the reaction with TLC, N-ethyl-N'-dimethylaminopropylcarbodiimide hydrochloride (34 mg, 0.18 mmol) and 1-hydroxybenzotriazole (24 mg, 0.18) was added to the reaction mixture under 0° C. and the mixture was stirred overnight under room temperature. The mixture was purified directly with an FSPE cartridge to afford LacβProNH—C$_8$F$_{17}$ (2) as a white solid (162 mg, qt.). $^1$H NMR (600 MHz, CD$_3$OD) δ 4.36 (d, 1 H, J=7.7 Hz), 4.30 (d, 1H, J=7.8 Hz), 3.92 (m, 2H), 3.87-3.74 (m, 3H), 3.70 (dd, 1H, J =11.4 Hz, 4.5 Hz), 3.66-3.46 (m, 7H), 3.41 (m, 1H), 3.38-3.20 (m, 2H), 2.52 (m, 4H), 1.85-1.75 (m, 2H). $^{13}$C (151 MHz, CD$_3$OD) δ 105.11, 104.17, 80.63, 77.09, 76.48, 76.43, 74.83, 74.76, 72.55, 70.30, 68.31, 62.50, 61.89, 37.80, 30.28, 27.77, 27.51. $^{19}$F (282 MHz, CD$_3$OD) δ −82.79 (s, 3F, CF$_3$), −116.18 (s, 2F, CF$_2$), −123.16 (s, 2F, CF$_2$), −123.31 (s, 2F, CF$_2$), −123.34 (s, 2F, CF$_2$), −124.17 (s, 2F, CF$_2$), −124.97 (s, 2F, CF$_2$), −127.72 (s, 2F, CF$_2$). HRMS (ESI) m/z calcd for [C$_{26}$H$_{32}$F$_{17}$NO$_{12}$+H]$^+$ 874.1726, found 874.1757.

Example 3

Synthesis of LacβProNH—C$_6$F$_{13}$ (3)

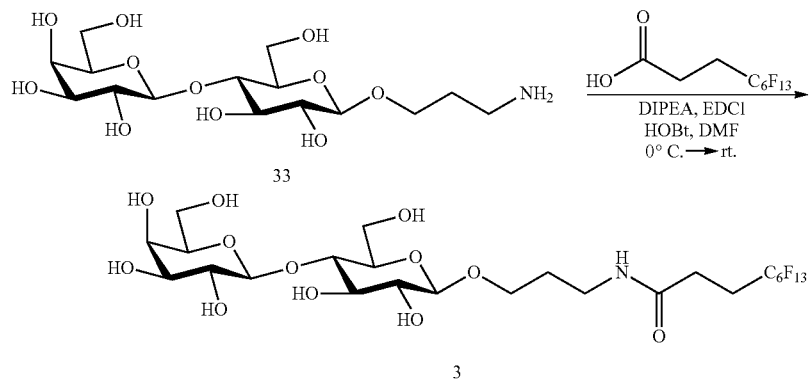

To a solution of LacβProNH$_2$ (33) (28 mg, 0.07 mmol), 2H, 2H, 3H, 3H-perfluorounonanoic acid (30 mg, 0.08 mmol), N-ethyl-N'-dimethylaminopropylcarbodiimide hydrochloride (17 mg, 0.09 mmol), and 1-hydroxybenzotriazole (10 mg, 0.08 mmol) in 5 mL anhydrous DMF, dry diisopropylethylamine (16 μL, 0.09 mmol) was added under argon atmosphere at 0° C. The mixture was allowed to slowly warm up to room temperature and stirred overnight. The mixture was purified directly with an FSPE cartridge and then with flash column chromatography (EtOAc:MeOH:H$_2$O=9:2:1 by volume) to afford LacβProNH—C$_6$F$_{13}$ 3 as a white solid (21 mg, 59%). $^1$H NMR (600 MHz, CD$_3$OD) δ 4.36 (d, 1H, J=7.7 Hz), 4.30 (d, 1H, J=7.8 Hz), 3.92 (m, 2H), 3.88-3.74 (m, 3H), 3.70 (dd, 1H, J=4.6 Hz and 11.5 Hz), 3.66-3.45 (m, 7H), 3.41 (m, 1H), 3.38-3.22 (m, 2H), 2.61-2.43 (m, 4H), 1.86-1.76 (m, 2H). $^{13}$C (151 MHz, CD$_3$OD) δ 172.75, 105.11, 104.16, 80.64, 77.08, 76.47, 76.42, 74.82, 74.76, 72.55, 70.29, 68.31, 62.50, 61.89, 37.80, 30.28, 27.75, 27.52. $^{19}$F (282 MHz, CD$_3$OD) δ -82.79 (s, 3F, CF$_3$), -116.18 (s, 2F, CF$_2$), -123.33 (s, 2F, CF$_2$), -124.17 (s, 2F, CF$_2$), -124.97 (s, 2F, CF$_2$), -127.72 (s, 2F, CF$_2$). HRMS (ESI) m/z calcd for [C$_{24}$H$_{32}$F$_{13}$NO$_{12}$+H]$_+$ 774.1790, found 774.1801.

Example 4

Synthesis of LacβProNH—C$_3$F$_7$ (4)

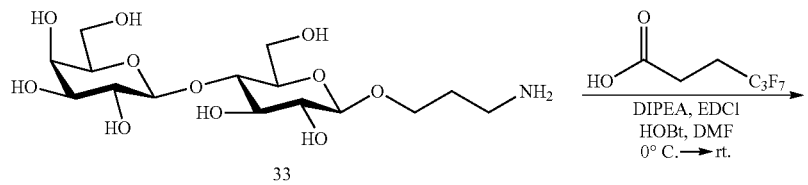

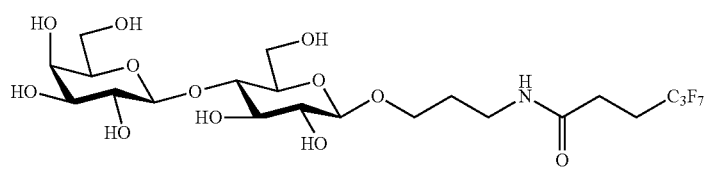

To a solution of LacβProNH$_2$ (33) (29 mg, 0.07 mmol), 2H, 2H, 3H, 3H-perfluorohexanoic acid (19 mg, 0.08 mmol), N-ethyl-N'-dimethylaminopropylcarbodiimide hydrochloride (18 mg, 0.09 mmol), and 1-hydroxybenzotriazole (11 mg, 0.08 mmol) in 5 ml anhydrous DMF, dry diisopropylethylamine (16 μL, 0.09 mmol) was added under argon atmosphere at 0° C. The mixture was allowed to slowly warm up to room temperature and stirred overnight. The mixture was purified directly with an FSPE cartridge and then with flash column chromatography (EtOAc:MeOH:H$_2$O=9:2:1 by volume) to produce LacβProNH—C$_3$F$_7$ (4) as a white solid (21 mg, 48%). $^1$H NMR (800 MHz, D$_2$O) δ 4.49 (d, 1H, J=8.0 Hz), 4.47 (d, 1H, J=7.8 Hz), 4.03-3.93 (m, 3H), 3.85-3.71 (m, 5H), 3.71-3.64 (m, 3H), 3.61 (s, 1H), 3.59-3.54 (m, 2H), 3.38-3.29 (m, 3H), 1.86 (p, 2H, J=6.5 Hz). $^{13}$C (201 MHz, D$_2$O) δ 173.72, 102.86, 102.00, 78.35, 75.28, 74.69, 74.30, 72.76, 72.45, 70.87, 68.47, 67.71, 60.93, 60.01, 36.28, 26.79. $^{19}$F (282 MHz, CD$_3$OD) δ −82.59 (s, 3F, CF$_3$), −117.17 (s, 2F, CF$_2$), −129.53 (s, 2F, CF$_2$). HRMS (ESI) m/z calcd for [C$_{21}$H$_{32}$F$_7$NO$_{12}$+H]$^+$ 624.1885, found 624.1894.

Example 5

Synthesis of LacβProNH-TEG-N$_3$ (34) and LacβProNH-HEG-N$_3$ (35)

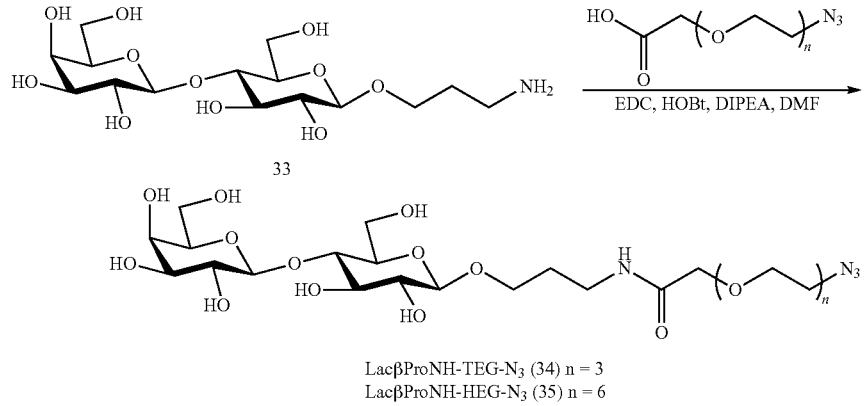

LacβProNH-TEG-N$_3$ (34) n = 3
LacβProNH-HEG-N$_3$ (35) n = 6

To a solution of LacβProNH$_2$ (33) (1 eq.) in anhydrous DMF, an ethylene glycol linker (11-azido-3,6,9-trioxaundecanoic acid or 20-azido-3,6,9,12,15,18-hexaoxaeicosanoic acid) (1.2 eq.) and N-hydroxybenzotriazole (HOBt, 2.0 eq.) were added. After being stirred for 30 mins, N-(3-dimethylaminopropyl)-N-ethylcarbodiimide hydrochloride (EDC, 2.0 eq.) and DIPEA (2.0 eq.) were added at 0° C. The mixture was stirred at 0° C. for 30 min. and then at room temperature for 24 h. After removed the solvent in vacuo, the residue was purified by flash column chromatography on silica gel (EtOAc:MeOH:H$_2$O=2:1:0.05 by volume) to produce the corresponding ethylene glycol-linked lactosides, LacβProNH-TEG-N$_3$ (34) and LacβProNH-HEG-N$_3$ (35) as white solids.

LacβProNH-TEG-N$_3$ (34): 1.17 g, 76%. $^1$H NMR (400 MHz, D$_2$O): δ 4.47 (d, 1H, J=8.0 Hz), 4.44 (d, 1H, J=7.8 Hz), 4.08 (s, 2H), 4.02-3.89 (m, 3H), 3.86-3.53 (m, 20H), 3.50 (t, 2H, J=4.8 Hz), 3.37 (t, 2H, J=6.8 Hz), 3.34-3.29 (m, 1H), 1.87 (p, 2H, J=6.5 Hz). $^{13}$C NMR (D$_2$O, 101 MHz): δ 172.56, 103.09, 102.23, 78.57, 75.50, 74.92, 74.51, 72.99, 72.67, 71.10, 70.46, 69.77, 69.69, 69.65 (2C), 69.39, 68.69, 67.93, 61.17, 60.25, 50.29, 36.10, 28.66. HRMS (ESI) m/z [M+H]$^+$ calcd for C$_{23}$H$_{43}$N$_4$O$_{15}$ 615.2725, found 615.2727; [M+Na]$^+$ C$_{23}$H$_{42}$N$_4$NaO$_{15}$ 637.2544, found 637.2539.

LacβProNH-HEG-N$_3$ (35): 0.82 g, 73%. $^1$H NMR (600 MHz, D$_2$O): δ 4.49 (d, 1H, J=7.8 Hz), 4.46 (d, 1H, J=8.4 Hz), 4.09 (s, 2H), 3.98-3.93 (m, 3H), 3.83-3.51 (m, 34H), 3.38 (t, 2H, J=6.6 Hz), 3.33 (t, 1H, J=8.4 Hz), 1.90-1.86 (m, 2H). $^{13}$C NMR (D$_2$O, 151 MHz): δ 172.35, 102.88, 102.02, 78.38, 75.30, 74.72, 74.31, 72.79, 72.47, 70.89, 70.24, 69.55, 69.53, 69.50, 69.48, 69.46, 69.16, 68.48, 68.05, 67.73, 60.95, 60.05, 50.09, 35.90, 28.47. HRMS (ESI) m/z [M+H]$^+$ calcd for C$_{29}$H$_{55}$N$_4$O$_{18}$ 747.3511, found 747.3518; [M+Na]$^+$ C$_{29}$H$_{54}$N$_4$NaO$_{18}$ 769.3331, found 769.3329.

Example 6

Synthesis of Fluorous-Tagged Acceptor Sugars 5-8 Containing Ethylene Glycol Linkers LacβProNH-TEG-N$_3$ (34) or LacβProNH-HEG-N$_3$ (35) (50-100 mg) was dissolved in 10 mL of H$_2$O/MeOH (1:1) and 50 mg Pd/C was added. The mixture was shaken under H$_2$ (4 Bar) for 2 h and filtered. The filtrate was evaporated to dryness to afford the corresponding amine product and used directly for the next coupling reaction. To a solution of corresponding amino-containing lactosides (TEG or HEG linker) (1.2 eq.) and HOBt (2.0 eq.) in 10 μL of dry DMF, EDC (2.0 eq.) and DIPEA (2.0 eq.) were added at 0° C. The mixture was stirred at 0° C. for 30 min and then at room temperature for overnight. The solvent was then removed in vacuo and the crude product was purified by flash column chromatography on silica gel (EtOAc:MeOH=2:1 by volume) to produce the corresponding fluorous-tagged oligosaccharides 5-8.

LacβProNH-TEG-C$_8$F$_{17}$ (5): 0.22 g, 68%. $^1$H NMR (800 MHz, D$_2$O): δ 4.44 (d, 1H, J=7.2 Hz), 4.43 (d, 1H, J=6.7 Hz), 4.01 (s, 2H), 3.98-3.86 (m, 3H), 3.86-3.46 (m, 20H), 3.45-3.24 (m, 5H), 2.63-2.28 (m, 4H), 1.90-1.76 (m, 2H). $^{13}$C NMR (D$_2$O, 201 MHz): δ 172.26, 171.83, 102.85, 102.09, 78.22, 75.21, 74.66, 74.26, 72.77, 72.46, 70.83, 70.06, 69.55, 69.47, 69.41, 69.38, 68.86, 68.47, 67.49, 60.89, 59.95, 38.93, 38.85, 35.80, 28.62, 26.18. $^{19}$F NMR (D$_2$O, 282 MHz): δ −83.81 (s, 3F, CF$_3$), −116.28 (s, 2F, CF$_2$), −123.33 to −124.89 (m, 10F, 5CF$_2$), −128.48 (s, 2F, CF$_2$). HRMS (ESI) m/z [M+H]$^+$ calcd for C$_{34}$H$_{48}$F$_{17}$N$_2$O$_{16}$ 1063.2732, found 1063.2744; [M+Na]$^+$ C$_{34}$H$_{47}$F$_{17}$N$_2$NaO$_{16}$ 1085.2552, found 1085.2543.

LacβProNH-HEG-C$_8$F$_{17}$ (6): 0.091 g, 67%. $^1$H NMR (800 MHz, D$_2$O): δ 4.48 (d, 1H, J=8.6 Hz), 4.47 (d, 1H,

J=8.5 Hz), 4.08 (s, 2H), 4.02-3.93 (m, 3H), 3.86-3.55 (m, 34H), 3.45-3.32 (m, 3H), 2.59-2.38 (m, 4H), 1.89 (p, 2H, J=6.4 Hz). $^{13}$C NMR (D$_2$O, 201 MHz): δ 172.03, 171.82, 102.92, 102.09, 78.45, 75.30, 74.72, 74.34, 72.81, 72.51, 70.89, 70.21, 69.65, 69.61, 69.57, 69.55, 69.51, 68.89, 68.49, 67.61, 60.96, 60.09, 38.98, 35.89, 28.64, 26.12. $^{19}$F NMR (D$_2$O, 282 MHz): δ −83.77 (s, 3F, CF$_3$), −116.29 (s, 2F, CF$_2$), −123.24 to −124.80 (m, 10F, 5CF$_2$), −128.44 (s, 2F, CF$_2$). HRMS (ESI) m/z [M+Na]$^+$ calcd for C$_{40}$H$_{59}$F$_{17}$N$_2$NaO$_{19}$ 1217.3338, found 1217.3301.

LacβProNH-TEG-C$_6$F$_{13}$ (7): 0.22 g, 70%. $^1$H NMR (800 MHz, D$_2$O): δ 4.43 (d, 2H, J=7.2 Hz), 4.01 (s, 2H), 3.98-3.88 (m, 3H), 3.83-3.51 (m, 20H), 3.42-3.27 (m, 5H), 2.58-2.35 (m, 4H), 1.89-1.78 (m, 2H). $^{13}$C NMR (D$_2$O, 201 MHz): δ 172.27, 171.89, 102.85, 102.07, 78.24, 75.22, 74.66, 74.27, 72.76, 72.45, 70.83, 70.07, 69.54, 69.47, 69.43, 69.36, 68.84, 68.45, 67.51, 60.89, 59.95, 38.91, 38.87, 35.79, 28.57, 26.17. $^{19}$F NMR (D$_2$O, 282 MHz): δ −83.50 (s, 3F, CF$_3$), −116.25 (s, 2F, CF$_2$), −123.51 (s, 2F, CF$_2$), −124.61 (s, 2F, CF$_2$), −125.00 (s, 2F, CF$_2$), −128.28 (s, 2F, CF$_2$). HRMS (ESI) m/z [M+H]$^+$ calcd for C$_{32}$H$_{48}$F$_{13}$N$_2$O$_{16}$ 963.2796, found 963.2809; [M+Na]$^+$ C$_{32}$H$_{47}$F$_{13}$N$_2$NaO$_{16}$ 985.2616, found 985.2602.

LacβProNH-HEG-C$_6$F$_{13}$ (8): 0.100 g, 66%. $^1$H NMR (600 MHz, D$_2$O): δ 8 4.47 (d, 1H, J=7.5 Hz), 4.46 (d, 1H, J=7.5 Hz), 4.06 (s, 2H), 4.02-3.91 (m, 3H), 3.88-3.48 (m, 34H), 3.45-3.28 (m, 3H), 2.59 -2.34 (m, 4H), 1.87 (p, 2H, J=6.6 Hz). $^{13}$C NMR (D$_2$O, 151 MHz): δ 172.24, 172.14, 103.09, 102.26, 78.61, 75.48, 74.90, 74.51, 72.97, 72.67, 71.07, 70.38, 69.80, 69.77, 69.74, 69.71, 69.65, 69.37, 69.33, 69.03, 68.66, 67.88, 67.79, 61.14, 60.25, 39.17, 36.06, 28.79, 26.31. $^{19}$F NMR (D$_2$O, 282 MHz): δ −83.42 (s, 3F, CF$_3$), −116.13 (s, 2F, CF$_2$), −123.45 (s, 2F, CF$_2$), −124.54 (s, 2F, CF$_2$), −124.86 (s, 2F, CF$_2$), −128.19 (s, 2F, CF$_2$). HRMS (ESI) m/z [M+H]$^+$ calcd for C$_{38}$H$_{60}$F$_{13}$N$_2$O$_{19}$ 1095.3583, found 1095.3550; [M+Na]$^+$ C$_{38}$H$_{59}$F$_{13}$N$_2$NaO$_{19}$ 1117.3402, found 1117.3374.

The synthesis of fluorous-tagged oligosaccharides 42-46 is set forth below.

Example 7

Synthesis of GlcNAcβ1-3LacβProNH-TEG-C$_8$F$_{17}$ (42b)

LacβProNH-TEG-C$_8$F$_{17}$ (88 mg, 1 eq.) and N-acetylglucosamine (37 mg, 2 eq.) were dissolved in water in a 50 mL centrifuge tube containing Tris-HCl buffer (100 mM, pH 8.0), ATP (137 mg, 3 eq.), UTP (146 mg, 3 eq.), and MgCl$_2$ (20 mM). After the addition of NahK (15 mg), GlmU (3 mg), NmLgtA (7 mg), and PmPpA (4 mg), millipore water was added to bring the total volume of the reaction mixture to 15 mL. The reaction was gently shaken in an isotherm incubator for 4 days at 37° C. After monitoring the reaction with TLC (EtOAc:MeOH: H$_2$O=5:2:1 by volume), which indicated the presence of ~10% of starting material, the reaction mixture was centrifuged (7000 rpm for 20 minutes) and the supernatant was purified directly via an FSPE cartridge. The collected methanol washes where concentrated and lyophilized. The lyophilized solid was re-dissolved in water with N-acetylglucosamine (20 mg), Tris-HCl buffer (100 mM, pH 8.0), ATP (80 mg), UTP (85 mg), and MgCl$_2$ (20 mM). After the addition of NahK (8 mg), GlmU (1.5 mg), NmLgtA (2.5 mg), and PmPpA (2 mg), millipore water was added to bring the total volume of the reaction mixture to 6 mL. After 29 h, the TLC showed full conversion of the starting material and the mixture was centrifuged and purified via FPSE. The methanol washes were concentrated and lyophilized to yield 42b as a white solid (96 mg, 92%).

Example 8

Synthesis of LacNAcβ1-3LacβProNH-TEG-C$_6$F$_{13}$ (43a)

A mixture of compound 42a (30 mg, 1 eq.), 300 µL water, 300 mM galactose (194 µL, 3 eq.), 200 mM ATP (292 µL, 2eq.), 200 mM UTP (292 µL, 2eq.), 1 M Tris-HCl buffer (200 µL, pH 7.5), 200 mM MgCl$_2$ (200 µL), GalK (0.29 mg), BLUSP (0.43 mg), NmLgtB (0.14 mg), and PmPpA (2.3 mg) were evenly distributed into two 1 mL Eppendorf tubes and gently shaken in an isotherm incubator at 37° C. The TLC (EtOAc:MeOH: H$_2$O=5:2:1 by volume) indicated the presence of ~15% starting material after 3 days. The reaction mixtures were then centrifuged (~13000 rpm for 10 minutes) and the supernatant was purified directly via an FSPE cartridge. The collected methanol washes where concentrated and lyophilized. The lyophilized solid was re-dissolved in in 80 µL water, 300 mM galactose (140 µL), 200 mM ATP (140 µL), 200 mM UTP (140 µL), 200 mM MgCl$_2$ (200 µL), GalK (0.29 mg), BLUSP (0.43 mg), NmLgtB (0.14 mg), and PmPpA (0.46 mg). The mixture was evenly distributed into two 1mL Eppendorf tubes and gently shaken at 37° C. After 2 days, the TLC indicated that the reaction was complete. The mixtures were centrifuged and the supernatants were directly purified via FSPE. The methanol washes were collected, concentrated, and lyophilized to produce 43a as a white solid (25 mg, 79%).

Example 9

Synthesis of LacNAcβ1-3LacβProNH-TEG-C$_8$F$_{17}$ (43b)

A mixture of compound 42b (32 mg, 1 eq.), 300 µL water, 300 mM galactose (252 µL, 3 eq.), 200 mM ATP (252 µL, 2eq.), 200 mM UTP (252 µL, 2 eq.), 1 M Tris-HCl buffer (200 µL, pH 7.5), 200 mM MgCl$_2$ (200 µL), GalK (0.29 mg), BLUSP (0.43 mg), NmLgtB (0.14 mg), and PmPpA (0.46 mg) were evenly distributed into two 1 mL Eppendorf tubes and gently shaken in an isotherm incubator at 37° C. The TLC (EtOAc:MeOH: H$_2$O=5:2:1 by volume) indicated the completion of the reaction after 2 days. The reaction mixtures were then centrifuged (13000 rpm for 10 minutes) and the supernatant was purified directly via an FSPE cartridge. The collected methanol washes where concentrated and lyophilized to afford 43b as a white solid (31 mg, 86%).

Example 10

Synthesis GlcNAcβ1-3LacNAcβ1-3LacβProNH-TEG-C$_6$F$_{13}$ (44a)

A mixture of compound 43a (10 mg, 1 eq.), 100 mM N-acetylglucosamine (450 µL, 6 eq.), 200 mM ATP (300 µL, 4eq.), 200 mM UTP (300 µL, 4eq.), 1 M Tris-HCl buffer (150 µL, pH 8.0), NahK (0.16 mg), GlmU (0.45 mg), NmLgtA (1.3 mg), and PmPpA (0.23 mg) was evenly distributed into three 1 mL Eppendorf tubes and gently shaken in an isotherm incubator at 37° C. Over the course of 4 days, the reaction was monitored with TLC (EtOAc: MeOH: H$_2$O=5:2:1 by volume) and additional ATP, UTP, LgtA, and PmPpA was added to the reaction until the starting material was completely consumed. The reaction mixtures was then centrifuged (13000 rpm for 10 minutes) and the supernatant was purified directly via an FSPE cartridge. The collected methanol washes where concentrated and lyophilized to produce 44a as a white solid (10 mg, 87%).

Example 11

Synthesis of GlcNAcβ1-3LacNAcβ1-3LacβProNH-TEG-$C_8F_{17}$ (44b)

Compound 43b (10 mg) underwent the exact procedures as the synthesis of 44a to produce 44b as a white solid (11 mg, 95%).

Example 12

Synthesis of (LacNAcβ1-3)$_2$LacβProNH-TEG-$C_6F_{13}$ (45a)

In a 1 mL Eppendorf tube, a mixture of compound 44a (8 mg, 1 eq.), 200 μL water, 200 mM galactose (53 μL, 2 eq.), 200 mM ATP (53 μL, 2 eq.), 200 mM UTP (53 μL, 2 eq.), 200 mM MgCl$_2$ (50 μL), GalK (0.07 mg), BLUSP (0.08 mg), NmLgtB (0.016 mg), PmPpA (0.26 mg), and Tris-HCl buffer (100 mM, pH 7.5) was gently shaken in an isotherm incubator at 37° C. Upon monitoring the reaction after 22 h via MALDI-TOF, an additional equivalent of both ATP and UTP, and BLUSP (0.056 mg) were added to the mixture. After 3 days, the MALDI-TOF indicated the full conversion of the product and the mixture was then centrifuged (13000 rpm for 10 minutes). The supernatant was purified directly via an FSPE cartridge. The collected methanol washes where concentrated and lyophilized to afford 45a as a white solid (9 mg, qt.).

Example 13

Synthesis of LacNAcβ1-3 )$_2$LacβProNH-TEG-$C_8F_{17}$ (45b)

In a 1 mL Eppendorf tube, a mixture of compound 44b (8 mg, 1 eq.), 150 μL water, 200 mM galactose (50 μL, 2 eq.), 200 mM ATP (75 μL, 3 eq.), 200 mM UTP (75 μL, 3 eq.), 200 mM MgCl$_2$ (50 μL), GalK (0.07 mg), BLUSP (0.13 mg), NmLgtB (0.016 mg), PmPpA (0.25 mg), and Tris-HCl buffer (100 mM, pH 7.5) was gently shaken in an isotherm incubator at 37° C. Upon monitoring the reaction after 26 h via MALDI-TOF, an additional equivalent of both ATP and UTP, and BLUSP (0.064 mg) were added to the mixture. After 2 days, the MALDI-TOF indicated the full conversion of the product and the mixture was then centrifuged (13000 rpm for 10 minutes). The supernatant was purified directly via an FSPE cartridge. The collected methanol washes where concentrated and lyophilized to afford 45b as a white solid (9 mg, qt.).

Example 14

Synthesis of (LacNAcβ1-3)$_3$LacβProNH-TEG-$C_6F_{13}$ (46)

In a 10 mL centrifuge tube, a mixture of LacβProNH-TEG-$C_6F_{13}$ 41a (1 mg, 1 eq.), Gal (10 mM, 20 eq.), GlcNAc (10 mM, 20 eq.), ATP (10 mM, 20 eq.), UTP (10 mM, 20 eq.), MgCl$_2$ (10 mM), Tris-HCl buffer (50 mM, pH 7.5), NahK (0.2 mg), GlmU (0.2 mg), NmLgtA (1.08 mg), GalK (0.05 mg), BLUSP (0.3 mg), NmLgtB (0.35 mg), and PmPpA (1.13 mg) was placed in an isotherm incubator under 37° C. with occasional gentle shaking After 2 days, MALDI-TOF monitoring of the reaction indicated the disappearance of 41a and GlcNAcβ1, 3LacNAc1-3LacβProNH-TEG-$C_6F_{13}$ and (LacNAcβ1-3)$_2$LacβProNH-TEG-$C_6F_{13}$ being the major products. The reaction mixture underwent centrifugation to remove the precipitates and the supernatant was purified with FSPE. The methanol washes were collected, lyophilized, and re-dissolved in water to undergo another round of the OP7E reaction with the exact conditions listed above. The reaction was monitored via MALDI-TOF and an additional 10 equivalents of ATP and UTP were added after 3 days. One day later, the reaction underwent centrifugation to remove all precipitates, and the supernatant was purified via FSPE. The methanol washes were collected, concentrated, and lyophilized to produce compound 46 as a white solid (2 mg, 95%). HPLC was performed on the product to obtain a pure NMR spectroscopy.

Exemplary one-pot multienzyme (OPME) glycosylation reactions are described below. Although particular enzymes are exemplified, one of ordinary skill in the art can readily adapt the reaction conditions for any of the glycotransferases disclosed herein. Reaction conversion rates were determined by staining the TLC plates with p-anisaldehyde sugar stain and then using ImageQuant 5.2 software to compare the relative intensities between the glycosylation product spot and the lactoside acceptor spot of each reaction (FIG. 1). For external standard comparison, each lactoside acceptor spot was also compared with its corresponding standard 10 mM stock solution spot to verify the conversion rates of each reaction.

Example 15

α2-3-Sialylation

PmST1 E271F/R313Y mutant (0.07 μg) was added to a 0.5 mL centrifuge tube containing 0.01 μmol of a lactoside acceptor (chosen from 1-8), Neu5Ac (1.2 eq.), CTP (2 eq.), Tris-HCl buffer (100 mM, pH 8.5), MgCl$_2$ (20 mM), NmCSS (0.08 μg), and water (total volume=10 μL). The reactions were monitored by TLC (EtOAc:MeOH:H$_2$O:AcOH=5:2:1:0.1).

Example 16

α2-6-Sialylation

Pd2,6ST (0.72 μg) was added to a 0.5 mL centrifuge tube containing 0.01 μmol (1 eq.) of a lactoside acceptor (chosen from 1-8), Neu5Ac (1.2 eq.), CTP (2 eq.), Tris-HCl buffer (100 mM, pH 8.5), MgCl$_2$ (20 mM), NmCSS (0.08 μg), and water (total volume=10 μL). The reactions were monitored by TLC (EtOAc:MeOH:H$_2$O:AcOH=5:2:1:0.1).

Example 17

α1-3-Galactosylation

α1-3GalT (0.4 μg) was added to a 0.5 mL centrifuge tube containing 0.01 μmol (1 eq.) of a lactoside acceptor (chosen from 1-8), galactose (1 eq.), ATP (2 eq.), UTP (2 eq.), MgCl$_2$ (20 mM), MnCl$_2$ (20 mM), Tris-HCl buffer (100 mM, pH=7.0), *E. coli* GalK (1.75 μg), BLUSP (4.3 μg), PmPpA (5.0 µg), and water (total volume=10 µL). The reactions were monitored by TLC (EtOAc:MeOH:H$_2$O=5:2:1).

Example 19

Preparative Scale Synthesis of Neu5Acα2-3LacβProNH-C$_6$F$_{13}$ (11)

LacβProNH-C$_6$F$_{13}$ (3) (10 mg, 1 eq.), Neu5Ac (5 mg, 1.2 eq.), and CTP (15 mg, 2 eq.) were dissolved in water in a 1 mL centrifuge tube containing Tris-HCl buffer (100 mM, pH 8.5) and MgCl$_2$ (20 mM). After the addition of PmST1_E271F/R313Y (0.033 mg) and NmCSS (0.2 mg), millipore water was added to bring the total volume of the reaction mixture to 1 mL. The reaction was gently shaken in an isotherm incubator for 2 h at 37° C. After monitoring the reaction with TLC (EtOAc:MeOH:H$_2$O=5:2:1 by volume), 0.5 eq. of additional CTP was added to the mixture. After another hour, 0.5 eq. of CTP was added again to drive the reaction towards completion. One hour later, the reaction underwent centrifugation to remove the precipitants. The supernatant was purified directly via an FSPE cartridge and concentrated to give 10 as a white solid (10 mg, 72%). $^1$H NMR (600 MHz, D$_2$O) δ 4.53 (d, 1H, J=7.8 Hz), 4.45 (d, 1H, J=7.9 Hz), 4.11 (d, 1H, J=8.0 Hz), 3.96 (m, 3H), 3.92-3.80 (m, 4H), 3.78-3.51 (m, 12H), 3.31 (d, 3H, J=7.8 Hz), 2.76 (dd, 1H, J=12.1 Hz, 4.1 Hz), 2.61-2.41 (m, 4H), 2.03 (s, 3H), 1.89-1.74 (m, 3H). $^{13}$C (201 MHz, CD$_3$OD) δ 174.05, 173.54, 171.31, 103.55, 102.66, 99.62, 79.34, 76.09, 75.55, 74.96, 74.78, 73.43, 73.26, 71.50, 69.33, 68.54, 67.83, 67.47, 66.78, 62.98, 61.24, 61.07, 60.39, 52.45, 40.59, 36.25, 28.80, 26.19 (dd, J=20.9 Hz and 42.7 Hz), 21.15. $^{19}$F (282 MHz, D$_2$O) δ −82.39 (s, 3F, CF$_3$), −115.64 (s, 2F, CF$_2$), −123.02 (s, 2F, CF$_2$), −124.04 (s, 2F, CF$_2$), −124.70 (s, 2F, CF$_2$), −127.42 (s, 2F, CF$_2$). HRMS (ESI) m/z calcd for [C$_{35}$H$_{48}$F$_{13}$N$_2$O$_{20}$]$^-$ 1063.2598, found 1063.2588.

Example 20

Preparative Scale Synthesis of Neu5Acα2-6LacβProNH-C$_6$F$_{13}$ (14)

LacβProNH-C$_6$F$_{13}$ (3) (10 mg, 1 eq.), Neu5Ac (5 mg, 1.2 eq.), and CTP (15 mg, 2 eq.) were dissolved in water in a 1 mL centrifuge tube containing Tris-HCl buffer (100 mM, pH 8.5) and MgCl$_2$ (20 mM). After the addition of Pd2,6ST (0.09 mg) and NmCSS (0.2 mg), millipore water was added to bring the total volume of the reaction mixture to 1 mL. The reaction was gently shaken in an isotherm incubator for 2 h at 37° C. After monitoring the reaction with TLC (EtOAc:MeOH:H$_2$O=5:2:1 by volume), 0.5 eq. of additional CTP was added to the mixture. After another hour, 0.5 eq. of CTP was added again to drive the reaction towards completion. One hour later, the reaction underwent centrifugation to remove the precipitants. The supernatant was purified directly via an FSPE cartridge and concentrated to produce 14 as a white solid (10 mg, 79%). $^1$H NMR (600 MHz, D$_2$O) δ 4.47 (d, 1H, J=7.7 Hz), 4.44 (d, 1H, J=7.5 Hz), 4.06-3.93 (m, 4H), 3.93-3.78 (m, 6H), 3.77-3.54 (m, 10H), 3.39-3.29 (m, 3H), 2.72 (dd, 1H, J=12.1, 4.0 Hz), 2.62-2.48 (m, 4H), 2.04 (s, 3H), 1.85 (p, 2H, J=6.0 Hz), 1.75 (t, 1H, J=12.1 Hz). $^{13}$C (151 MHz, D$_2$O) δ 174.84, 173.41, 103.18, 101.95, 100.24, 79.54, 74.57, 73.61, 72.68, 72.47, 72.33, 71.72, 70.74, 68.45, 68.32, 67.61, 65.45, 62.58, 61.74, 60.17, 57.97, 51.74, 40.04, 36.28, 28.32, 26.74, 26.43, 22.00. $^{19}$F (282 MHz, D$_2$O) δ −81.92 (s, 3F, CF$_3$), −115.34 (s, 2F, CF$_2$), −122.81 (s, 2F, CF$_2$), −123.78 (s, 2F, CF$_2$), −124.54 (s, 2F, CF$_2$), −127.07 (s, 2F, CF$_2$). HRMS (ESI) m/z calcd for [C$_{35}$H$_{48}$F$_{13}$N$_2$O$_{20}$]$^-$ 1063.2598, found 1063.2588.

Example 21

Preparative Scale Synthesis of Galα1-3LacβProNH-TEG-C$_8$F$_{17}$ (23)

LacβProNH-TEG-C$_8$F$_{17}$ (5) (11 mg, 1 eq.) and galactose (1.5 eq.) were dissolved in water in a 1 mL centrifuge tube containing Tris-HCl buffer (100 mM, pH 7.0), ATP (2 eq.), UTP (2 eq.), MgCl$_2$ (10 mM), and MnCl$_2$ (10 mM). After the addition of E. coli GalK (1 mg), BLUSP (0.2 mg), α1-3GalT (0.08 mg), and PmPpA (0.25 mg), millipore water was added to bring the total volume of the reaction mixture to 1 mL. The reaction was gently shaken in an isotherm incubator for 16 h at 37° C. After monitoring the reaction with TLC (EtOAc:MeOH:H$_2$O=5:2:1 by volume), an additional amount of ATP (0.5 eq.), UTP (0.5 eq.), EcGalK (0.5 mg), BLUSP (0.05 mg), α1-3GalT (0.02 mg), and PmPpA (0.05 mg) was added to the mixture. After another 17 h, the reaction was still incomplete and the mixture was purified directly via an FSPE cartridge and concentrated to go through another round of the enzymatic reaction as described above to drive the reaction towards completion. The reaction underwent centrifugation to remove the precipitates and was purified using FSPE to produce 23 as a white solid (10 mg, 82%). $^1$H NMR (600 MHz, D$_2$O) δ 5.18 (d, 1H, J=2.9 Hz), 4.54 (d, 1H, J=7.5 Hz), 4.46 (d, 1H, J=7.7 Hz), 4.27-4.13 (m, 2H), 4.10-3.91 (m, 6H), 3.91-3.45 (m, 23H), 3.45-3.26 (m, 5H), 3.59-2.30 (m, 4H), 1.90-1.76 (m, 2H). $^{13}$C (151 MHz, D$_2$O) δ 172.01, 171.77, 102.78, 102.06, 95.24, 78.62, 77.01, 74.91, 74.60, 74.32, 72.69, 70.67, 70.06, 69.49, 69.40, 69.15, 68.98, 68.85, 68.09, 67.48, 64.64, 62.34, 60.89, 60.79, 60.05, 56.84, 38.90, 35.82, 28.63, 26.14. $^{19}$F (282 MHz, D$_2$O) δ −83.76 (s, 3F, CF$_3$), −116.31 (s, 2F, CF$_2$), −123.32 (s, 2F, CF$_2$), −123.70 (m, 4F, 2CF$_2$), −124.68 (s, 2F, CF$_2$), −124.94 (s, 2F, CF$_2$), −128.46 (s, 2F, CF$_2$). HRMS (ESI) m/z calcd for [C$_{40}$H$_{57}$F$_{17}$N$_2$O$_{21}$+H]$^+$ 1225.3481, found 1225.3481.

Example 22

Preparative Scale Synthesis of Neu5Acα2-3LacβProNH-TEG-C$_6$F$_{13}$ (25)

LacβProNH-TEG-C$_6$F$_{13}$ (7) (10 mg, 1 eq.), Neu5Ac (1.2 eq.), and CTP (2 eq.) were dissolved in water in a 1 mL centrifuge tube containing Tris-HCl buffer (100 mM, pH 8.5) and MgCl$_2$ (20 mM). After the addition of PmST1_E271F/R313Y mutant (0.033 mg) and NmCSS (0.2 mg), millipore water was added to bring the total volume of the reaction mixture to 1 mL. The reaction was gently shaken in an isotherm incubator for 2 h at 37° C. After monitoring the reaction with TLC (EtOAc:MeOH:H$_2$O=5:2:1 by volume), 0.5 eq. of additional CTP was added to the mixture. After another hour, 0.5 eq. of CTP was added again to drive the reaction towards completion. After 1 h, the reaction mixture was purified directly via an FSPE cartridge and concentrated by rotavap to produce compound 25 as a white solid (14 mg, 86%). $^1$H NMR (800 MHz, D$_2$O) δ 4.55 (d, 1H, J=7.8 Hz), 4.48 (d, 1H, J=7.9 Hz), 4.13 (dd, 1H, J=2.3 Hz and 9.8 Hz), 4.07 (s, 2H), 4.03-3.94 (m, 3H), 3.94-3.81 (m, 4H), 3.81-3.55 (m, 22H), 3.43 (t, 2H, J=5.1 Hz), 3.37 (t, 2H, J=6.9 Hz), 3.34 (t, 1H, J=8.3 Hz), 2.78 (dd, 1H, J=4.4 Hz and 12.4 Hz), 2.59 (t, 2H, J=7.0 Hz), 2.54 (dd, 2H, J=6.8. Hz and 18.8 Hz), 2.06 (s, 3H), 1.88 (p, 2H, J=6.7

Hz), 1.83 (t, 1H, J=12.1). $^{13}$C (201 MHz, D$_2$O) δ 174.92, 173.83, 173.21, 172.14, 102.61, 102.07, 99.75, 78.26, 75.41, 75.07, 74.70, 74.29, 72.81, 72.76, 71.67, 70.16, 69.57, 69.47, 69.32, 69.30, 68.75, 68.29, 68.03, 67.64, 67.41, 62.50, 61.27, 60.94, 60.01, 58.59, 51.63, 39.55, 38.97, 35.85, 28.49, 26.47 (d, J=49.1 Hz), 21.97. $^{19}$F (282 MHz, D$_2$O) δ −82.78 (s, 3F, CF$_3$), −115.82 (s, 2F, CF$_2$), −123.17 (s, 2F, CF$_2$), −124.23 (s, 2F, CF$_2$), −124.78 (s, 2F, CF$_2$), −127.73 (s, 2F, CF$_2$). HRMS (ESI) m/z calcd for [C$_{43}$H$_{63}$F$_{13}$N$_3$O$_{24}$]$^-$ 1252.3599, found 1252.3586.

Example 23

Preparative Scale Synthesis of Neu5Acα2-6LacβProNH-TEG-C$_6$F$_{13}$ (27)

LacβProNH-TEG-C$_6$F$_{13}$ (7) (10 mg, 1 eq.), Neu5Ac (5 mg, 1.2 eq.), and CTP (15 mg, 2 eq.) were dissolved in water in a 1 mL centrifuge tube containing Tris-HCl buffer (100 mM, pH 8.5) and MgCl$_2$ (20 mM). After the addition of Pd2,6ST (0.09 mg) and NmCSS (0.2 mg), millipore water was added to bring the total volume of the reaction mixture to 1 mL. The reaction was gently shaken in an isotherm incubator for 2 h at 37° C. After monitoring the reaction with TLC (EtOAc:MeOH:H$_2$O=5:2:1 by volume), 0.5 eq. of additional CTP was added to the mixture. After another hour, 0.5 eq. of CTP was added again to drive the reaction towards completion. After 1 h, the reaction was purified directly by passing through an FSPE cartridge and concentrated by rotavap to produce 27 as a white solid (13 mg, qt.). $^1$H NMR (600 MHz, D$_2$O) δ 4.46 (d, 1H, J=7.8 Hz), 4.42 (d, 1H, J=7.7 Hz), 4.05 (s, 2H), 4.00-3.77 (m, 8H), 3.74-3.49 (m, 22H), 3.43-3.29 (m, 5H), 2.71 (dd, 1H, J=4.4 Hz and 12.1 Hz), 2.62-2.43 (m, 4H), 2.02 (s, 3H), 1.90-1.81 (m, 2H), 1.73 (t, 1H, J=12.2 Hz). $^{13}$C (151 MHz, D$_2$O) δ 174.80, 173.40, 173.20, 172.14, 103.18, 101.93, 100.22, 79.57, 74.57, 73.59, 72.67, 72.46, 72.30, 71.71, 70.72, 70.16, 69.57, 69.49, 69.46, 69.32, 68.75, 68.43, 68.29, 68.27, 67.63, 63.43, 62.56, 62.22, 60.18, 57.27, 51.73, 40.05, 38.96, 35.86, 28.51, 26.59, 21.99. $^{19}$F (282 MHz, D$_2$O) δ −82.48 (s, 3F, CF$_3$), −115.63 (s, 2F, CF$_2$), −123.04 (s, 2F, CF$_2$), −124.07 (s, 2F, CF$_2$), −124.72 (s, 2F, CF$_2$), −127.50 (s, 2F, CF$_2$). HRMS (ESI) m/z calcd for [C$_{43}$H$_{63}$F$_{13}$N$_3$O$_{24}$]$^-$ 1252.3599, found 1252.3599.

Example 24

Preparative Scale Synthesis of Galα1-3LacβCProNH-TEG-C$_6$F$_{13}$ (29)

LacβProNH-TEG-C$_6$F$_{13}$ (7) (12 mg, 1 eq.) and galactose (1.5 eq.) were dissolved in water in a 1 mL centrifuge tube containing Tris-HCl buffer (100 mM, pH 7.0), ATP (2 eq.), UTP (2 eq.), MgCl$_2$ (10 mM), and MnCl$_2$ (10 mM). After the addition of E. coli GalK (1 mg), BLUSP (0.2 mg), α1-3GalT (0.16 mg), and PmPpA (0.25 mg), millipore water was added to bring the total volume of the reaction mixture to 1 mL. The reaction was gently shaken in an isotherm incubator for 16 h at 37° C. After monitoring the reaction with TLC (EtOAc:MeOH:H$_2$O=5:2:1 by volume), an additional amount of ATP (0.5 eq.), UTP (0.5 eq.), EcGalK (0.5 mg), BLUSP (0.1 mg), α1-3GalT (0.04 mg), and PmPpA (0.25 mg) was added to the mixture. After another 19 h, more ATP (0.1 eq.), UTP (0.1 eq.), EcGalK (0.2 mg), BLUSP (0.01 mg), α1-3GalT (0.004 mg), and PmPpA (0.025 mg) was added to the mixture. After 36 h, the reaction was purified directly via an FSPE cartridge and concentrated to produce 29 as a white solid (13 mg, 89%). $^1$H NMR (800 MHz, D$_2$O) δ 5.17 (d, 1H, J=3.3 Hz), 4.54 (d, 1H, J=7.7 Hz), 4.48 (d, 1H, J=7.6 Hz), 4.27-4.16 (m, 2H), 4.11-3.93 (m, 6H), 3.89 (dd, 1H, J=3.3 Hz and 10.3 Hz), 3.86-3.48 (m, 22H), 3.46-3.30 (m, 5H), 2.60-2.35 (m, 4H), 1.88 (p, 2H, J=6.2 Hz). $^{13}$C (201 MHz, D$_2$O) δ 172.22, 171.90, 102.86, 102.13, 95.36, 78.75, 77.17, 74.98, 74.69, 74.41, 72.77, 70.76, 70.16, 69.61, 69.56, 69.50, 69.43, 69.25, 69.08, 68.89, 68.16, 67.59, 64.75, 62.61, 60.94, 60.88, 60.16, 56.76, 38.97, 35.91, 28.68, 26.20. $^{19}$F (282 MHz, D$_2$O) δ −83.32 (s, 3F, CF$_3$), −116.14 (s, 2F, CF$_2$), −123.44 (s, 2F, CF$_2$), −124.51 (s, 2F, CF$_2$), −124.93 (s, 2F, CF$_2$), −128.13 (s, 2F, CF$_2$). HRMS (ESI) m/z calcd for [C$_{38}$H$_{57}$F$_{13}$N$_2$O$_{21}$+H]$^+$ 1125.3319, found 1125.3351.

Example 25

Fluorous Solid-Phase Extraction (FSPE) Cartridge Purification

For fluorous-solid phase extractions, the chemical reaction mixtures were directly loaded to FluoroFlash® SPE cartridges (2 g fluorous silica gel in 10 mL cartridge, conditioned with deionized water) (Fluorous Tech. Inc.) and washed with deionized water (3 mL×4) to remove non-fluorous reaction components. The fluorous-tagged products were eluted with methanol (3 mL×4). For enzymatic reactions, the reaction mixtures were centrifuged at 13,226×g for 10 min. to remove precipitates. Next, the supernatants were loaded to the conditioned FSPE cartridges and the cartridges were then washed with deionized water (3 mL×4) to remove non-fluorous components. Lastly, the fluorous-tagged products were eluted by the following washes of methanol (3 mL×4).

Example 26

Preparation of GM$_3$Sph From LacβSph

Figure 6:
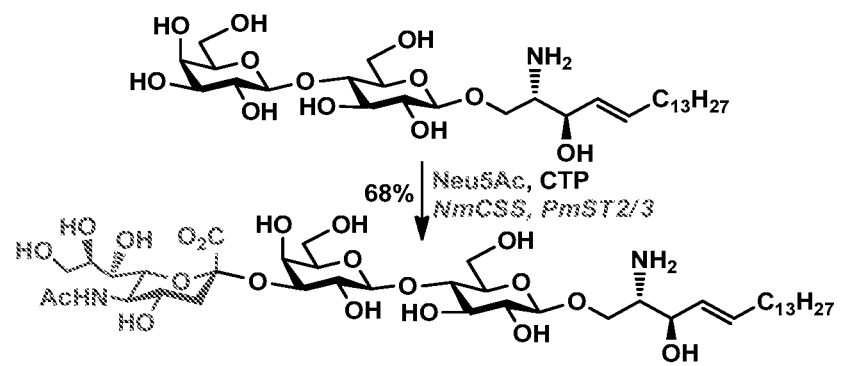
FIG. 6 shows one-pot multienzyme synthesis of GM3 glycosphingosine from LacβSph.
Figure 7:
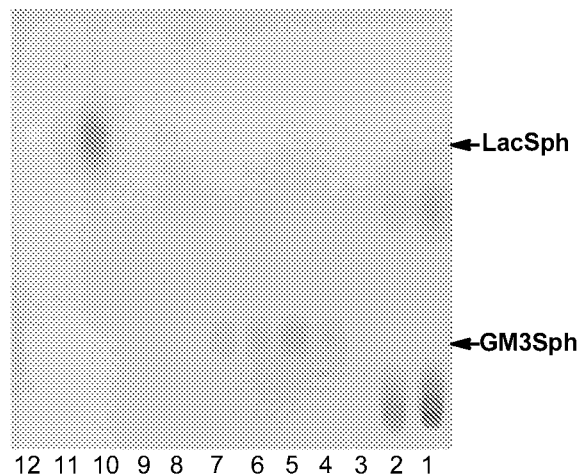
FIG. 7 shows C18 cartridge purification of gangliosphingosines from enzymatic reactions for preparation of GM₃Sph. TLC was developed using EtOAc:MeOH:H₂O:HOAc=5:1:0.8:0.1, v/v. Eluant for fractions: 1, flow through; 2-3, water; 4-9, 60% MeOH in water; 10-12, MeOH.

The inventive method has been successfully tested in synthesizing and purifying GM$_3$ sphingosine (GM$_3$Sph) from the reaction mixture of a one-pot two-enzyme reaction containing NmCSS and PmST2 or PmST3 using LacβSph as an acceptor (FIG. 6). Upon the completion of the enzymatic reaction monitored by TLC, the reaction mixture was centrifuged (to remove precipitates generated during the reaction) and the supernatant was directly loaded onto a C18 SPE cartridge (Supelco), washed with water, and eluted with water-methanol gradient solution. The unreacted N-acetylneuraminic acid (Neu5Ac, the most common form of sialic acid), CMP-Neu5Ac, CTP, byproduct CMP, and salts were completely removed from the cartridge during the water washing step. The GM$_3$ sphingosine was readily obtained by eluting the C18 SPE cartridge with 60% MeOH in H$_2$O. The remaining LacβSph was readily eluted using MeOH (FIG. 7). The purification process took less than 10 minutes, in contrast to the several hours using standard silica gel chromatography. Thus, the use of C18 cartridgs for purification and isolation allows for fast and efficient separation of glycolipids from non-lipid components in the reaction mixture, as well as allowing for the effective separation of the product and the acceptor, both of which are glycolipids.

Solid-phase extraction (SPE) C18 cartridges are available from various commercial sources (e.g. Sigma-Aldrich). The loading capacity of SPE C18 cartridges is around 5-10% by the weight of C18 silica gel). For example, the loading capacity of a 12 mL C18 cartridge containing 2 g silica gel was 100 mg for GM$_3$-sphingosine. The elute solvent mixtures containing different ratios of H$_2$O, MeOH, and CH$_3$CN commonly used for solid-phase extraction will be tested for glycosphingolipids. The C18 cartridge can be cleaned and regenerated by washing thoroughly with methanol and reused for many times.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of preparing an isolated glycosphingosine, comprising:
   (a) forming a reaction mixture comprising an acceptor having a sugar component covalently linked to a sphingosine moiety, a donor having a sugar component, and a glycosyltransferase, under conditions suitable to form a glycosidic bond between the sugar component of the acceptor and the sugar component of the donor to form a glycosphingosine; and
   isolating the glycosphingosine by a process consisting of optional step (a1), step (b), and step (c):
   (a1) optionally centrifuging the reaction mixture to remove precipitates generated during the step (a), thereby forming a supernatant comprising the glycosphingosine;
   (b) applying the reaction mixture of step (a) or the supernatant of step (a1) directly to a solid-phase extraction (SPE) cartridge; and
   (c) eluting the glycosphingosine from the SPE cartridge, thereby yielding the isolated glycosphingosine,
   wherein the solid-phase extraction cartridge is selected from the group consisting of a fluorous solid phase extraction cartridge and a C18 solid phase extraction cartridge, and
   wherein the isolated glycosphingosine is yielded in a molar yield of at least 65%.

2. The method of claim 1, wherein the donor is a nucleoside phosphate comprising a monosaccharide selected from the group consisting of Gal, Neu5A, GlcNAc, GalNAc, Fuc, GlcA, GalA and Neu5Ac.

3. The method of claim 1, wherein the donor is selected from the group consisting of uridine 5'-diphosphate-galactose (UDP-Gal) and cytidine 5'-monophosphate-N-acetylneuraminic acid (CMP-Neu5Ac).

4. The method of claim 1, wherein the acceptor has the structure:

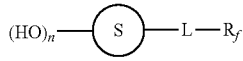

wherein
S is a monosaccharide, disaccharide or oligosaccharide;
L is a covalent bond;
R$_f$ is the sphingosine moiety; and
subscript n is an integer from 3 to 20.

5. The method of claim 4, wherein the acceptor has the structure:

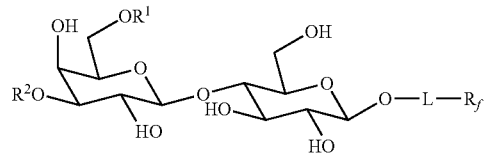

wherein R$^1$ and R$^2$ are each H.

6. The method of claim 4, wherein the isolated glycosphingosine has the structure:

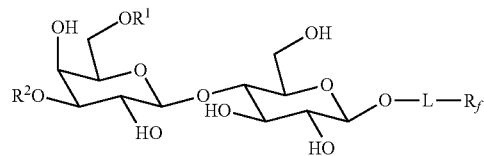

wherein R$^1$ and R$^2$ are each independently selected from the group consisting of hydrogen, Fucα1-2, GlcNAcβ1-3, (Galβ1-4GlcNAc)$_{1-5}$β1-3, (Galβ1-3GlcNAc)$_{1-5}$β1-3, Galα1-3, Galα1-4, GalNAcβ1-4, Galβ1-3GalNAcβ1-4, Siaα2-3Galβ1-3GalNAcβ1-4, Siaα2-3, Siaα2-8Siaα2-3, Siaα2-8Siaα2-8Siaα2-3, and Siaα2-6, such that at least one of R$^1$ and R$^2$ is other than hydrogen.

7. The method of claim 6, wherein:
   (a) R$^1$ is hydrogen and R$^2$ is Neu5Acα2-3,
   (b) R$^1$ is Neu5Acα2-6 and R$^2$ is hydrogen, or
   (c) R$^1$ is hydrogen and R$^2$ is Galα1-3.

8. The method of claim 1, wherein the glycosyltransferase is selected from the group consisting of a sialyltransferase, a fucosyltransferase, a mannosyltransferase, a galactosyltransferase, a glucosyltransferase, an N-acetylgalactosaminyltransferase, an N-acetylglucosaminyltransferase, a glucouronyltransferase, and a xylosyltransferase.

9. The method of claim 1, wherein the glycosyltransferase is selected from the group consisting of PmST1 E271F/R313Y, Pd2-6ST, α1-3GalT, PmST1 M144D, PmST1, PmST2, PmST3, Psp2-6ST, Cst-I, Cst-II, α2-3SiaT, α2-6SiaT, α2-8SiaT, α2-9SiaT, α1-2FucT, α1-3FucT, α1-4FucT, α1-6FucT, α1-2ManT, α1-3ManT, α1-4ManT, α1-6ManT, β1-2ManT, β1-4ManT, α1-2GalT, α1-3GalT, α1-4GalT, α1-6GalT, β1-2GalT, β1-3 GalT, β1-4GalT, α1-2GlcT, α1-3 GlcT, α1-4GlcT, α1-6GlcT, β1-2GlcT, β1-3GlcT, β1-4GlcT, β1-6GlcT, α1-3GalNAcT, β1-4GalNAcT, α1-4GalNAcT, β1-3GalNAcT, α1-2GlcNAcT, α1-3GlcNAcT, α1-4GlcNAcT, α1-6GlcNAcT, β1-2GlcNAcT, β1-3GlcNAcT, β1-4GlcNAcT, β1-6GlcNAcT, β1-3GlcAT, β1-4GlcAT, α1-3Xyl, α1-6Xyl, and β1-2Xyl.

10. The method of claim 1, wherein the donor is selected from the group consisting of cytidine 5'-monophosphate (CMP)-sialic acid, a guanosine 5'-diphosphate(GDP)-fucose, guanosine 5'-diphosphate(GDP)-mannose, uridine 5'-diphosphate(UDP)-galactose, uridine 5'-diphosphate(UDP)-glucose, uridine 5'-diphosphate(UDP)-N-acetylgalactosamine, a uridine 5'-diphosphate(UDP)-N-acetylglucosamine, uridine 5'-diphosphate(UDP)-glucuronic acid, and uridine 5'-diphosphate(UDP)-xylose.

11. The method of claim 1, wherein the solid-phase extraction cartridge is a fluorous SPE cartridge.

12. The method of claim 1, wherein the solid-phase extraction cartridge is a C18 SPE cartridge.

13. The method of claim 1, wherein steps (a1), (b), and (c) are conducted in less than ten minutes.

14. The method of claim 1, wherein the solid-phase extraction cartridge is a C18 SPE cartridge; and wherein steps (a1), (b), and (c) are conducted in less than ten minutes.

* * * * *